(12) United States Patent
Makra

(10) Patent No.: US 8,772,273 B2
(45) Date of Patent: Jul. 8, 2014

(54) FORMULATIONS AND USES OF RETINOIC ACID RECEPTOR SELECTIVE AGONISTS

(75) Inventor: Ferenc Makra, Palo Alto, CA (US)

(73) Assignee: QuRetino Therapeutics, Inc., Palo Alto, CA (US)

( * ) Notice: Subject to any disclaimer, the term of this patent is extended or adjusted under 35 U.S.C. 154(b) by 14 days.

(21) Appl. No.: 13/253,014

(22) Filed: Oct. 4, 2011

(65) Prior Publication Data

US 2013/0085166 A1 Apr. 4, 2013

(51) Int. Cl.
| | | |
|---|---|---|
| *A01N 43/00* | (2006.01) | |
| *A61K 31/19* | (2006.01) | |
| *A61K 31/35* | (2006.01) | |
| *A61K 31/21* | (2006.01) | |
| *A61K 9/14* | (2006.01) | |

(52) U.S. Cl.
USPC ........... 514/183; 514/569; 514/456; 514/510; 424/484

(58) Field of Classification Search
None
See application file for complete search history.

(56) References Cited

U.S. PATENT DOCUMENTS

| 5,556,844 A * | 9/1996 | Reichert et al. ........... 514/171 |
| 2005/0113447 A1* | 5/2005 | Belloni et al. ........... 514/469 |
| 2006/0280715 A1* | 12/2006 | Vishnupad et al. ........ 424/70.13 |

FOREIGN PATENT DOCUMENTS

| WO | WO 92/06948 A1 | 4/1992 |
| WO | WO 99/33821 A1 | 7/1999 |
| WO | WO 0109076 A2 | 2/2001 |
| WO | WO 03062230 A1 | 7/2003 |

OTHER PUBLICATIONS

Jain, S., Journal of Dermatological Treatment (2004) 15, pp. 200-207.*
International Search Report and Written Opinion for PCT/US2012/058726, issued May 7, 2013.

* cited by examiner

*Primary Examiner* — Scott Long
*Assistant Examiner* — Lyndsey Beckhardt
(74) *Attorney, Agent, or Firm* — Morgan, Lewis & Bockius LLP

(57) ABSTRACT

The invention provides retinoic acid receptor (RAR) selective agonists and formulations thereof for the treatment of disease or for inducing a medically beneficial effect.

11 Claims, No Drawings

FORMULATIONS AND USES OF RETINOIC ACID RECEPTOR SELECTIVE AGONISTS

FIELD OF THE INVENTION

This invention relates to retinoic acid receptor (RAR) selective retinoid agonists and to the use of such retinoic acid receptor agonists, particularly retinoic acid receptor γ (RARγ) selective agonists for the treatment of a disease and for inducement of a medically beneficial effect.

BACKGROUND OF THE INVENTION

Retinoids are a class of compounds structurally related to vitamin A, comprising natural and synthetic compounds. Several series of retinoids have been found clinically useful in the treatment of dermatological and oncological diseases. Retinoic acid and its other naturally occurring retinoid analogs (9-cis retinoic acid, all-trans 3,4-didehydro retinoic acid, 4-oxo retinoic acid and retinol) are pleiotropic regulatory compounds that modulate the structure and function of a wide variety of inflammatory, immune and structural cells. They are important regulators of epithelial cell proliferation, differentiation and morphogenesis in lungs. Retinoids exert their biological effects through a series of hormone nuclear receptors that are ligand inducible transcription factors belonging to the steroid/thyroid receptor super family.

The retinoid receptors are classified into two families, the retinoic acid receptors (RARs) and the retinoid X receptors (RXRs), each consisting of three distinct subtypes (α, β, and γ). Each subtype of the RAR gene family encodes a variable number of isoforms arising from differential splicing of two primary RNA transcripts. All-trans retinoic acid is the physiological hormone for the retinoic acid receptors and binds with approximately equal affinity to all the three RAR subtypes, but does not bind to the RXR receptors for which 9-cis retinoic acid is the natural ligand.

Retinoids have anti-inflammatory effects, alter the progression of epithelial cell differentiation, and inhibit stromal cell matrix production. These properties have led to the development of topical and systemic retinoid therapeutics for dermatological disorders such as psoriasis, acne, and hypertrophic cutaneous scars. Other applications include the control of acute promyelocytic leukemia, adeno- and squamous cell carcinoma, and hepatic fibrosis.

A limitation in the therapeutic use of retinoids outside of cancer has stemmed from the relative toxicity observed with the naturally occurring retinoids, all-trans retinoic acid and 9-cis retinoic acid. These natural ligands are non-selective and therefore have pleiotropic effects throughout the body, which are often toxic.

Recently various retinoids have been described that interact selectively or specifically with the RAR or RXR receptors or with specific subtypes (α, β, γ) within a class. For example, Tom et al., *Archives of Dermatology*, 2005, 141: 1373-1377, describe the efficacy and safety of short contact administration of topical tretinoin on foot ulcers in patients with diabetes.

SUMMARY OF THE INVENTION

The invention provides novel formulations and uses of RAR selective agonists. A RAR selective agonist, a pharmaceutically acceptable salt of a RAR selective agonist or a formulation of either of these may be used to treat a subject suffering from one or more diseases disclosed herein or to induce a medically beneficial effect in a subject. Exemplary RAR selective retinoid agonists have a structure according to formula I:

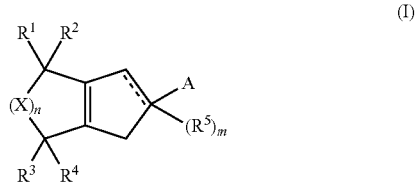

(I)

wherein the dotted bond is either present and forms a double bond, or is absent; $R^1$, $R^2$, $R^3$ and $R^4$ are independently hydrogen or alkyl; n is 1, 2 or 3; X is —C($R^8$)($R^9$)— for n=1, 2 or 3; or X is oxygen for n=1; $R^8$ and $R^9$ are independently hydrogen or alkyl; $R^5$ is hydrogen, alkyl, alkoxy, alkoxy-alkyl-, alkylthio, alkyl-$NR^{10}$—, alkenyl, alkenyloxy, alkynyl, benzyl, cycloalkyl-alkyl, phenyl-alkyl, $R^{10}$ is hydrogen or alkyl; m is 0 when the dotted bond is present; and m is 1 when the dotted bond is absent; and A is a residue of formula:

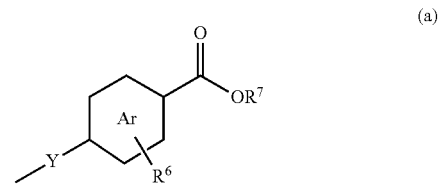

(a)

or of formula:

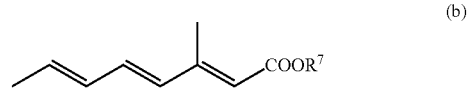

(b)

wherein Ar is phenyl or a heteroarylic ring; $R^6$ is hydrogen, halogen, alkoxy or hydroxy; $R^7$ is hydrogen or alkyl; and Y is —COO—, —OCO—, —CONR$^{10}$—, —NR$^{10}$CO—, —CH=CH—, —C≡C—, —COCH=CH—, —CHOHCH=CH—, —CH$_2$O—, —CH$_2$S—, —CH$_2$SO—, —CH$_2$SO$_2$—, —CH$_2$NR$^{10}$—, —OCH$_2$—, —SCH$_2$—, —SOCH$_2$—, —SO$_2$CH$_2$— or —NR$^{10}$CH$_2$—, with the proviso that when Y is —OCO—, —NR$^{10}$CO—, —OCH$_2$—, —SCH$_2$—, —SOCH$_2$—, —SO$_2$CH$_2$— or —NR$^{10}$CH$_2$—, $R^5$ is hydrogen, alkyl, alkoxy-alkyl-, alkenyl, alkynyl, benzyl, cycloalkyl-alkyl or phenyl-alkyl; and pharmaceutically active salts of carboxylic acids of formula I. Exemplary formulations of the RAR selective agonist are suitable for topical or oral administration.

Also provided are devices containing the RAR selective agonist or a formulation thereof for delivery of the compound.

The RAR selective agonists and formulations disclosed herein may be used to treat a variety of diseases or to induce a variety of medically beneficial effects. One advantage possessed by a number of the embodiments disclosed herein is the lower toxicity and fewer side effects experienced by subjects undergoing treatment with the compounds and compositions as compared to the toxicity and side effects engendered by other retinoids known in the art. Various embodiments of the invention are more stable than known RAR selective agonists and formulations and may also provide more cost effective treatments in treating a disease.

DETAILED DESCRIPTION OF THE INVENTION

The present invention provides compounds and pharmaceutical formulations suitable for administering one or more therapeutic agents to a subject, pharmaceutical products containing the same, processes of preparing such pharmaceutical formulations and products, and methods of treating a subject employing such pharmaceutical formulations and products.

Compounds

Various RAR selective agonists known in the art may be used in the formulations and methods described herein. Exemplary compounds useful in making the pharmaceutical formulations and in practicing the methods of treatment and prevention disclosed herein are RAR selective agonists having structures according to Formula I and the various other compounds based on this structure, including pharmaceutically acceptable salts thereof

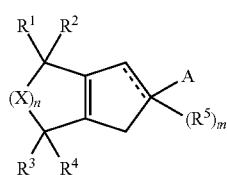

(I)

wherein the dotted bond is either present and forms a double bond, or is absent; $R^1$, $R^2$, $R^3$ and $R^4$ are independently hydrogen or alkyl; n is 1, 2 or 3; X is —$C(R^8)(R^9)$— for n=1, 2 or 3; or X is oxygen for n=1; $R^8$ and $R^9$ are independently hydrogen or alkyl; $R^5$ is hydrogen, alkyl, alkoxy, alkoxy-alkyl-, alkylthio, alkyl-$NR^{10}$—, alkenyl, alkenyloxy, alkynyl, benzyl, cycloalkyl-alkyl, phenyl-alkyl, $R^{10}$ is hydrogen or alkyl; m is 0 when the dotted bond is present; and m is 1 when the dotted bond is absent; and A is a residue of formula:

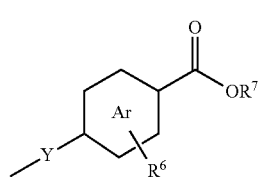

(a)

or of formula:

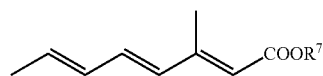

(b)

wherein Ar is phenyl or a heteroarylic ring; $R^6$ is hydrogen, halogen, alkoxy or hydroxy; $R^7$ is hydrogen or alkyl; and Y is —COO—, —OCO—, —$CONR^{10}$—, —$NR^{10}CO$—, —CH=CH—, —C≡C—, —COCH=CH—, —CHOHCH=CH—, —$CH_2O$—, —$CH_2S$—, —$CH_2SO$—, —$CH_2SO_2$—, —$CH_2NR^{10}$—, —$OCH_2$—, —$SCH_2$—, —$SOCH_2$—, —$SO_2CH_2$— or —$NR^{10}CH_2$—, with the proviso that when Y is —OCO—, —$NR^{10}CO$—, —$OCH_2$—, —$SCH_2$—, —$SOCH_2$—, —$SO_2CH_2$— or —$NR^{10}CH_2$—, $R^5$ is hydrogen, alkyl, alkoxy-alkyl-, alkenyl, alkynyl, benzyl, cycloalkyl-alkyl or phenyl-alkyl; and pharmaceutically active salts of carboxylic acids of formula I.

The term "alkyl" as used herein denotes straight chain or branched alkyl residues containing 1 to 10, preferably 1 to 7 carbon atoms, such as methyl, ethyl, isobutyl, pentyl, amyl and 3-pentyl, hexyl, heptyl, and the like; the alkyl chain may be substituted by amino, hydroxy, halogen. Such groups are for example hydroxymethyl, 2-hydroxyethyl, 3-hydroxypropyl, 4-hydroxybutyl, aminomethyl, 2-aminoethyl and the like.

As used herein, the term "alkoxy" refers to a straight or branched chain hydrocarbonoxy group wherein the "alkyl" portion is an alkyl group as defined above. Examples include methoxy, ethoxy, n-propoxy and the like.

As used herein, the term "alkoxy-alkyl-" refers to a dialkylether residue such as methoxymethyl, methoxyethyl, methoxypropyl, ethoxymethyl, ethoxyethyl, methoxy-ethoxymethyl and the like.

As used herein, the term "alkylthio" refers to a straight or branched chain hydrocarbonthio group wherein the "alkyl" portion is an alkyl group as defined above. Examples include methylthio, ethylthio, propylthio, and the like.

As used herein the term "alkenyl" refers to a straight or branched hydrocarbon chain radical having from 2 to 8 carbon atoms, preferably from 2 to 4 carbon atoms, and having at least one olefinic double bond, e.g. allyl, vinyl etc.

As used herein, the term "alkenyloxy" refers to a straight or branched chain hydrocarbonoxy group wherein the "alkenyl" portion is an alkenyl group as defined above. Examples include allyloxy, 3-butenyloxy and the like.

As used herein the term "alkynyl" refers to a straight or branched hydrocarbon chain radical having from 2 to 8 carbon atoms, preferably from 2 to 4 carbon atoms, and having at least one triple bond.

The term "cycloalkyl-alkyl" as used herein refers to alkyl groups as defined above bearing a cycloalkyl group having 3 to 7 carbon atoms as for example cyclopropylmethyl, cyclobutylmethyl, cyclopentylmethyl, cyclohexylmethyl, cyclopropylethyl, cyclobutylethyl, cyclopentylethyl, cyclohexylethyl and the like.

As used herein the term "phenyl-alkyl" refers to a alkyl group as defined above having a phenyl group attached to the terminal C-atom as benzyl, phenethyl, phenylpropyl and the like, the phenyl group may unsubstituted or substituted by alkyl or alkoxy.

The term "heteroarylic ring" as used herein refers to a 5 or 6-membered heteroaryl ring containing at least one hetero atom selected from oxygen, sulfur, and nitrogen, for example, pyridinyl, furanyl or thiophenyl. In formulae I, I-1 and IA-IH, "Ar" surrounded by hexagon, also referred to as simply "Ar", can indicate a heteroarylic ring having at least three ring carbon atoms, in which case the heteroarylic ring is bonded to each of Y, $R^6$ and —$C(O)OR^7$ via a different ring carbon atom. Alternatively, Ar surrounded by hexagon can indicate phenyl, in which case Y and —$C(O)OR^7$ are para to each other.

The groups Y are shown in their orientation in the compound of formula I. By way of illustration, when Y is —$CONR^{10}$—, the nitrogen is bonded directly to the group Ar.

For groups having acidic protons, an ionized or salt form is equally contemplated. For example, —COOH also refers to —$COO^-$ and —COOM, while —OH also refers to —$O^-$ and —OM, where M is a cation.

The compounds of formula I, wherein $R^7$ is hydrogen, form salts with pharmaceutically acceptable bases such as alkali salts, e.g. Na- and K-salts, and ammonium or substituted ammonium salts such as trimethylammonium salts, which are within the scope of this invention.

When n is 2 or 3 in the formulae given in this application, each occurrence of $R^8$ can be the same or different and each occurrence of $R^9$ can be the same or different. It is preferred that all occurrences of $R^8$ are the same as the others and that all occurrences of $R^9$ are the same as the others. When n is 1, 2 or 3, it is most preferred for each $R^8$ and each $R^9$ to be hydrogen. In exemplary embodiments, n is 2.

In some embodiments, $R^1$, $R^2$, $R^3$ and $R^4$ are independently selected alkyl. In exemplary embodiments, $R^1$, $R^2$, $R^3$ and $R^4$ are methyl.

In some embodiments, $R^5$ is alkyl. In exemplary embodiments, $R^5$ is pentyl.

In exemplary embodiments, Ar surrounded by hexagon is phenyl.

In exemplary embodiments, $R^6$ is H. In exemplary embodiments, $R^7$ is H. In exemplary embodiments, $R^8$ is H. In exemplary embodiments, $R^9$ is H.

In exemplary embodiments, Y is —C(O)(O)—.

An exemplary RAR selective agonist has the structure:

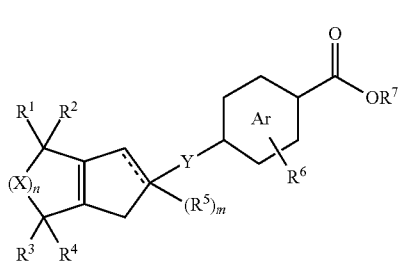

I-1 wherein the dotted bond is present and forms a double bond, or is absent; $R^1$, $R^2$, $R^3$ and $R^4$ are independently hydrogen or alkyl; n is 1, 2, or 3; X is —C($R^8$)($R^9$)— for n=1, 2 or 3; or X is oxygen for n=1; $R^5$ is hydrogen, alkyl, alkoxy, alkenyl, alkenyloxy, alkynyl, benzyl, cycloalkyl-alkyl or phenylalkyl; m is 0 when the dotted bond is present; or m is 1 when the dotted bond is absent; Ar is phenyl or heteroarylic ring; $R^6$ is hydrogen, halogen, alkoxy or hydroxy; $R^7$ is hydrogen or alkyl; $R^8$ and $R^9$ are independently hydrogen or alkyl; and Y is —COO—, —OCO—, —CONH—, —NHCO—, —CH=CH—, —C≡C—, —COCH=CH—, —CHOHCH=CH—, —CH$_2$O—, —CH$_2$S— or —CH$_2$NH—; with the proviso that when Y is —OCO— or —NHCO—, $R^5$ is hydrogen, alkyl, alkenyl, alkynyl, benzyl, cycloalkyl-alkyl or phenylalkyl; or a pharmaceutically active salt of Formula I-1.

A RAR selective agonist also refers to a pharmaceutically active salt of Formula I or any subgenus or species thereof. Exemplary salts are salts of a carboxylic acid of Formula I. The terms "pharmaceutically acceptable salts" and "pharmaceutically active salt", used interchangeably herein, are meant to include salts of the compounds of the invention that are prepared with nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic and the like. Also included are salts of amino acids such as arginate and the like, and salts of organic acids like glucuronic or galactunoric acids and the like. See, for example, Berge et al., Journal of Pharmaceutical Science, 1977, 66: 1-19. Certain specific compounds of the present invention contain both basic and acidic functionalities that allow the compounds to be converted into either base or acid addition salts.

Especially preferred are the compounds of formulas:

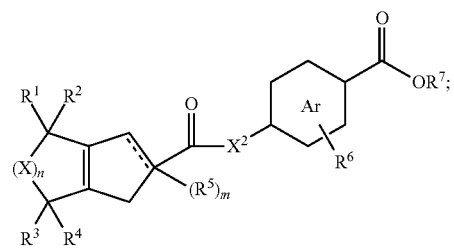

IA

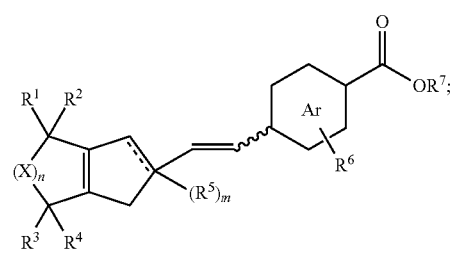

IB

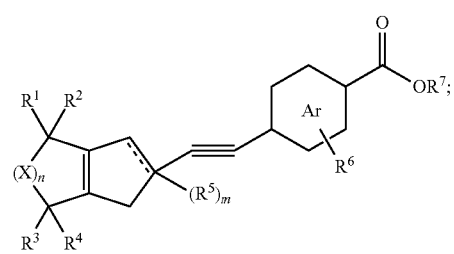

IC

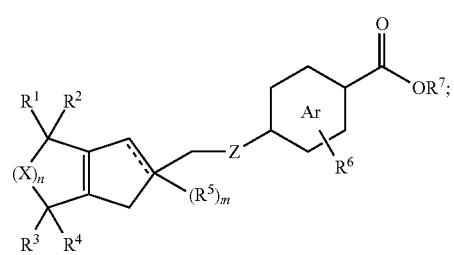

ID

-continued

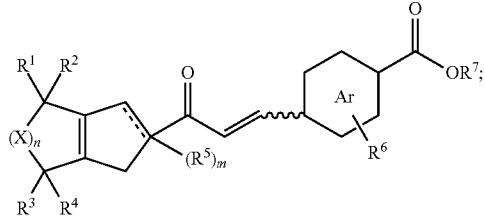
IE

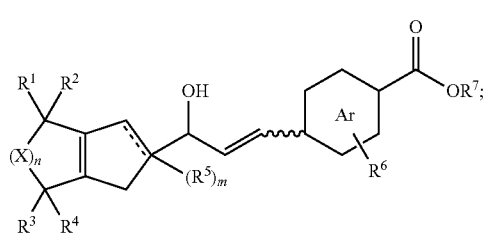
IF

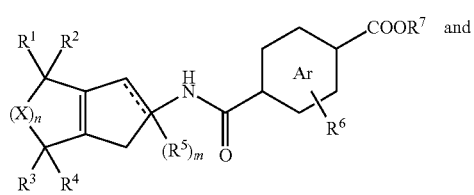
IG

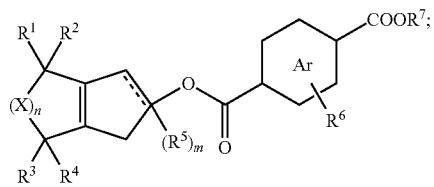
IH wherein the symbols are as defined above, $X^2$ is oxygen or —NH—, and Z is oxygen, sulfur or —NH—; and pharmaceutically active salts of carboxylic acids of formulae IA-IH.

In exemplary embodiments, n is 2. In exemplary embodiments, $X^2$ is oxygen.

The double bond in compounds of formulae IB, IE and IF may form an E/Z mixture or be E or Z configurated, preferably E configurated. The zigzag line in these formulae above indicates that the configuration can be E or Z.

Preferred compounds are those wherein X is —C($R^8$)($R^9$)— and n is an integer 1 or 2. In some embodiments, $R^8$ and $R^9$ are the same. In exemplary embodiments, $R^8$ and $R^9$ are H.

In some embodiments, $R^1$, $R^2$, $R^3$ and $R^4$ are independently selected alkyl. In exemplary embodiments, $R^1$, $R^2$, $R^3$ and $R^4$ are methyl.

In some embodiments, $R^5$ is alkyl. In exemplary embodiments, $R^5$ is pentyl.

In exemplary embodiments, Ar surrounded by hexagon is phenyl.

In exemplary embodiments, $R^6$ is H. In exemplary embodiments, $R^7$ is H. In exemplary embodiments, $R^8$ is H. In exemplary embodiments, $R^9$ is H.

Especially preferred are compounds of formula IA wherein $X^2$ is oxygen and n is 2, for example:

A  4,4,7,7-tetramethyl-2,3,4,5,6,7-hexahydro-1H-indene-2-carboxylic acid 4-carboxy-phenyl ester

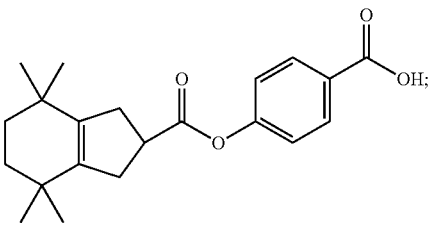 [SMILES: CC1(C)CCC(C)(C)C2=C1CC(C(=O)Oc1ccc(C(=O)O)cc1)C2]

B  2,4,4,7,7-pentamethyl-2,3,4,5,6,7-hexahydro-1H-indene-2-carb oxylic acid 4-carboxy-phenyl ester

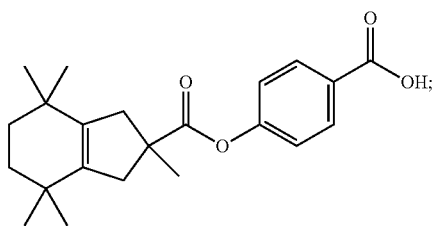 [SMILES: CC1(C)CCC(C)(C)C2=C1CC(C)(C(=O)Oc1ccc(C(=O)O)cc1)C2]

C  2-ethyl-4,4,7,7-tetramethyl-2,3,4,5,6,7-hexahydro-1H-indene-2-carboxylic acid 4-carboxy-phenyl ester

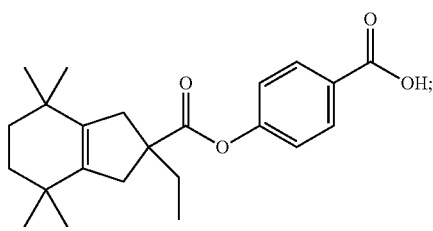 [SMILES: CCC1(C(=O)Oc2ccc(C(=O)O)cc2)CC2=C(C1)C(C)(C)CCC2(C)C]

D  4,4,7,7-tetramethyl-2-pentyl-2,3,4,5,6,7-hexahydro-1H-indene-2-carboxylic acid 4-carboxy-phenyl ester

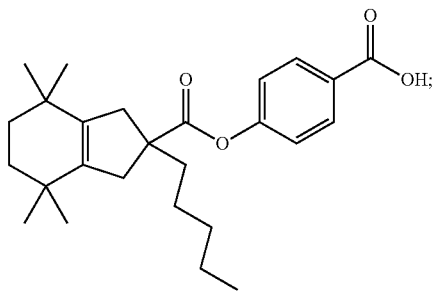 [SMILES: CCCCCC1(C(=O)Oc2ccc(C(=O)O)cc2)CC2=C(C1)C(C)(C)CCC2(C)C]

E  2-benzyl-4,4,7,7-tetramethyl-2,3,4,5,6,7-hexahydro-1H-indene-2-carboxylic acid 4-carboxy-phenyl ester

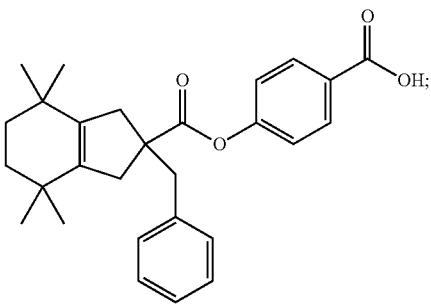 [SMILES: CC1(C)CCC(C)(C)C2=C1CC(Cc1ccccc1)(C(=O)Oc1ccc(C(=O)O)cc1)C2]

2-propyl-4,4,7,7-tetramethyl-2,3,4,5,6,7-hexahydro-1H-indene-2-carboxylic acid 4-carboxy-phenyl ester;
2-butyl-4,4,7,7-tetramethyl-2,3,4,5,6,7-hexahydro-1H-indene-2-carboxylic acid 4-carboxy-phenyl ester;
2-hexyl-4,4,7,7-tetramethyl-2,3,4,5,6,7-hexahydro-1H-indene-2-carboxylic acid 4-carboxy-phenyl ester and
2-phenethyl-4,4,7,7-tetramethyl-2,3,4,5,6,7-hexahydro-1H-indene-2-carboxylic acid 4-carboxy-phenyl ester.

Further preferred are compounds of formula IA wherein Ar is pyridine, i.e.,
6-[(4,4,7,7-tetramethyl-2-pentyl-2,3,4,5,6,7-hexahydro-1H-indene-2-carbonyl)-amino]-nicotinic acid

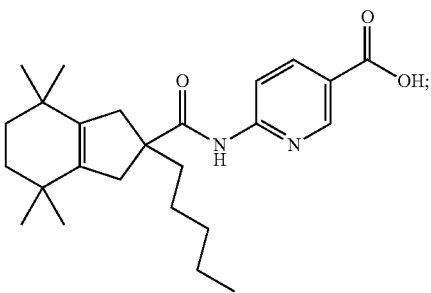 [SMILES: CCCCCC1(C(=O)Nc2ccc(C(=O)O)cn2)CC2=C(C1)C(C)(C)CCC2(C)C]

Further preferred are compounds of formula IA wherein n is 1 and X is —C(R$^8$)(R$^9$)—:
4,4,6,6-tetramethyl-2-pentyl-1,2,3,4,5,6-hexahydro-pentalene-2-carboxylic acid 4-carboxy-phenyl ester;
and compounds wherein n is 1 and X is oxygen:
1,1,3,3-tetramethyl-5-pentyl-3,4,5,6-tetrahydro-1H-cyclopenta[c]furan-5-carboxylic acid 4-carboxy-phenyl ester.

A further group of preferred compounds are compounds
a) of formula IB:
4-[2-(4,4,7,7-tetramethyl-2-pentyl-2,3,4,5,6,7-hexahydro-1H-inden-2-yl)-vinyl]-benzoic acid;

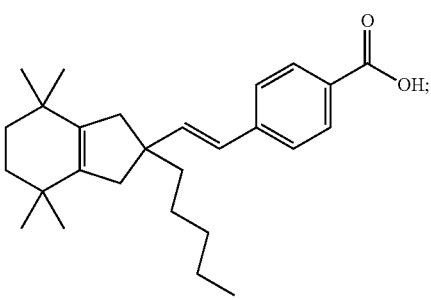 [SMILES: CCCCCC1(/C=C/c2ccc(C(=O)O)cc2)CC2=C(C1)C(C)(C)CCC2(C)C]

b) of formula IC:
4-(4,4,7,7-tetramethyl-2-pentyl-2,3,4,5,6,7-hexahydro-1H-indene-2-ylethynyl)-benzoic acid

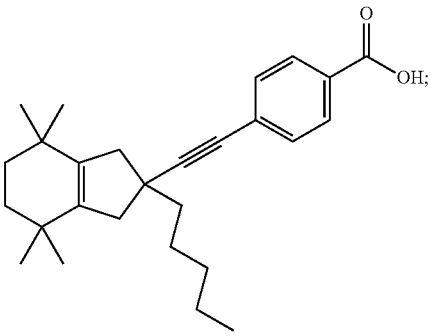 [SMILES: CCCCCC1(C#Cc2ccc(C(=O)O)cc2)CC2=C(C1)C(C)(C)CCC2(C)C]

c) of formula ID, wherein Z is oxygen:
4-(4,4,7,7-tetramethyl-2-pentyl-2,3,4,5,6,7-hexahydro-1H-inden-2-ylmethoxy)-benzoic acid;

of formula ID, wherein Z is sulfur:
4-(4,4,7,7-tetramethyl-2-pentyl-2,3,4,5,6,7-hexahydro-1H-inden-2-ylmethylsulfanyl)-benzoic acid; and of formula ID, wherein Z is —NH—:
4-[-(4,4,7,7-tetramethyl-2-pentyl-2,3,4,5,6,7-hexahydro-1H-inden-2-ylmethyl)-amino]-benzoic acid;

d) of formula IE:
4-[3-oxo-3-(4,4,7,7-tetramethyl-2-pentyl-2,3,4,5,6,7-hexahydro-1H-indene-2-yl)-propenyl]-benzoic acid; and e) of formula IF:
4-[3-hydroxy-3-(4,4,7,7-tetramethyl-2-pentyl-2,3,4,5,6,7-hexahydro-1H-inden-2-yl)-propenyl]-benzoic acid.

Further preferred compounds of formula I are the compounds of formula

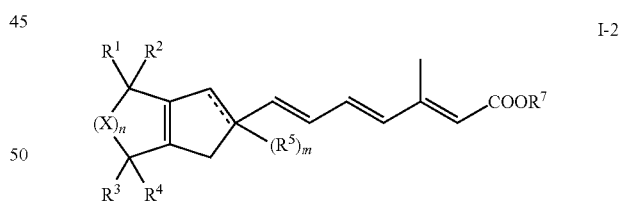

I-2 wherein the dotted bond is present and forms a double bond, or is absent; R$^1$, R$^2$, R$^3$, R$^4$ are independently hydrogen or alkyl; n is 1, 2 or 3; X is —C(R$^8$)(R$^9$)— for n=1, 2 or 3; or X is oxygen for n=1; R$^8$ and R$^9$ are independently hydrogen or alkyl; R$^5$ is hydrogen, alkyl, alkoxy, alkenyl, alkenyloxy, alkynyl, benzyl, cycloalkyl-alkyl, phenyl-alkyl; m is 0 when the dotted bond is present; or m is 1 when the dotted bond is absent; and R$^7$ is hydrogen or alkyl; and pharmaceutically active salts of carboxylic acids of formula I-2.

Especially preferred compounds of formula I-2 are
(2E,4E,6E)-3-methyl-7-(4,4,7,7-tetramethyl-2-pentyl-2,3,4,5,6,7-hexahydro-1H-inden-2-yl)-hepta-2,4,6-trienoic acid

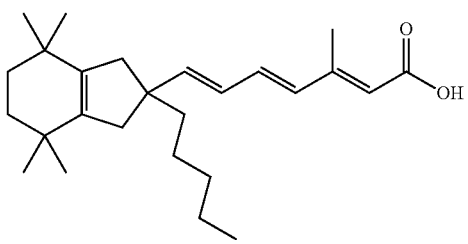 [SMILES: CCCCCC1(/C=C/C=C/C(C)=C/C(=O)O)CC2=C(C1)C(C)(C)CCC2(C)C]

and
(2Z,4E,6E)-3-methyl-7-(4,4,7,7-tetramethyl-2-pentyl-2,3,4,5,6,7-hexahydro-1H-inden-2-yl)-hepta-2,4,6-trienoic acid

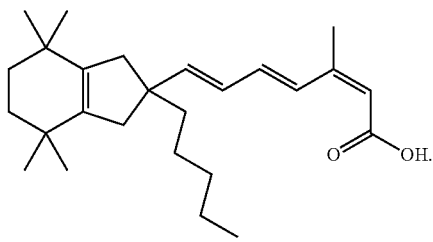 [SMILES: CCCCCC1(/C=C/C=C/C(C)=C\C(=O)O)CC2=C(C1)C(C)(C)CCC2(C)C]

In some embodiments, a compound has the structure:

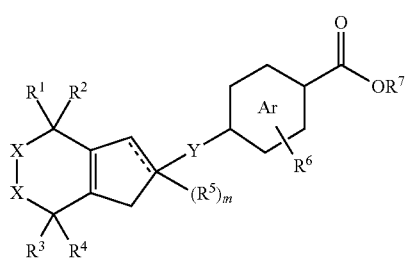

wherein the dotted bond is either present and forms a double bond, or is absent; $R^1, R^2, R^3, R^4$ are independently hydrogen or alkyl; X is $-C(R^8)(R^9)-$; each $R^8$ and each $R^9$ is independently hydrogen or alkyl; $R^5$ is hydrogen, alkyl, alkoxy, alkoxy-alkyl-, alkylthio, alkyl-$NR^{10}-$, alkenyl, alkenyloxy, alkynyl, benzyl, cycloalkyl-alkyl, or phenyl-alkyl; $R^{10}$ is hydrogen or alkyl; m is 0 when the dotted bond is present; and m is 1 when the dotted bond is absent; and Ar surrounded by hexagon shown above is phenyl and Y and $-C(O)OR^7$ are para to each other; $R^6$ is hydrogen, halogen, alkoxy or hydroxy; $R^7$ is hydrogen or alkyl; and Y is $-COO-$, $-OCO-$, $-CONR^{10}-$, $-NR^{10}CO-$, $-CH=CH-$, $-C\equiv C-$, $-COCH=CH-$, $-CHOHCH=CH-$, $-CH_2O-$, $-CH_2S-$, $-CH_2SO-$, $-CH_2SO_2-$, $-CH_2NR^{10}-$, $-OCH_2-$, $-SCH_2-$, $-SOCH_2-$, $-SO_2CH_2-$ or $-NR^{10}CH_2-$, with the proviso that when Y is $-OCO-$, $-NR^{10}CO-$, $-OCH_2-$, $-SCH_2-$, $-SOCH_2-$, $-SO_2CH_2-$ or $-NR^{10}CH_2-$, $R^5$ is hydrogen, alkyl, alkoxy-alkyl-, alkenyl, alkynyl, benzyl, cycloalkyl-alkyl or phenyl-alkyl; or where $R^7$ is hydrogen, a pharmaceutically active salt of the compound.

In some embodiments, $R^1, R^2, R^3, R^4$ are alkyl. In exemplary embodiments, $R^1, R^2, R^3, R^4$ are methyl.

In some embodiments, each $R^8$ is the same and each $R^9$ is the same. In some embodiments, each $R^8$ is hydrogen and each $R^9$ is hydrogen. In some embodiments, $R^5$ is hydrogen, alkyl, alkoxy, alkenyl, alkenyloxy, alkynyl, benzyl, cycloalkyl-alkyl or phenylalkyl; $R^{10}$ is hydrogen; Y is $-COO-$, $-OCO-$, $-CONR^{10}-$, $-NR^{10}CO-$, $-CH=CH-$, $-C\equiv C-$, $-COCH=CH-$, $-CHOHCH=CH-$, $-CH_2O-$, $-CH_2S-$, or $-CH_2NR^{10}-$, with the proviso that when Y is $-OCO-$ or $-NR^{10}CO-$, $R^5$ is hydrogen, alkyl, alkenyl, alkynyl, benzyl, cycloalkyl-alkyl or phenylalkyl. In some embodiments, Y is $-COO-$ or $-CONR^{10}$. In some embodiments, Y is $-COO-$.

Synthesis

The compounds according to the invention can be prepared in a manner known in the art. In particular, compounds of formula IA, wherein $X^2$ is oxygen or $-NH-$ may for example be prepared according to scheme 1:

SCHEME 1

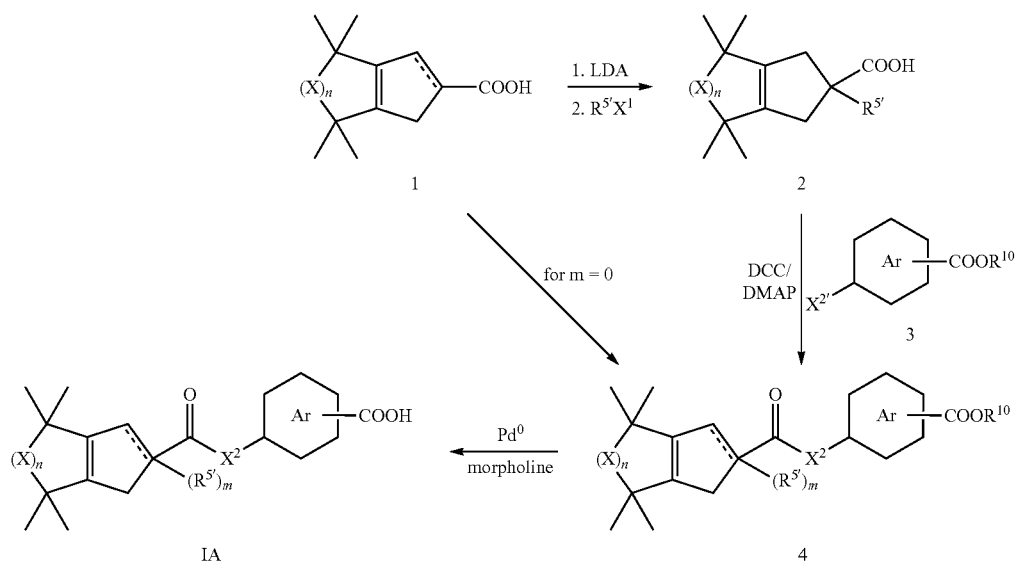

wherein X, n, m and Ar are defined as above and $R^5$ is hydrogen, alkyl, alkoxy-alkyl-, alkenyl, alkynyl, benzyl, cycloalkyl-alkyl, phenyl-alkyl; $X^1$ is a halogen, preferably bromide or iodide; $X^{2'}$ is —OH or $NH_2$; $X^2$ is oxygen or —NH—; and $R^{10}$ is $R^7$ or a carboxylic acid protecting group, preferably an allylic group. LDA is lithium diisopropylamide; and DCC/DMAP is dicyclohexylcarbodiimide/dimethylamino pyridine.

The acid 1, wherein the dotted line is absent and thus m is 1, can be alkylated with a suitable alkylhalogenide preferably an alkylbromide or an alkyliodide, or with an alkyl sulfonate, e.g. tosylate or mesylate, using a strong base, e.g. lithium diisopropylamide or potassium tert-butylate, to give the alkylated acid 2, which is condensed with a hydroxy- or aminoaryl carboxylic acid ester 3 to give compound 4. In the alternative the alkylation step is omitted for compounds of formula IA, wherein the dotted bond is present and m is thus 0. As condensation agent dicyclohexylcarbodiimide/4-dimethylaminopyridine can be used. Alternatively the acid 2 (or 1, respectively) can be transformed into the acid chloride (thionyl chloride, oxalyl chloride) and then reacted with compounds 3 and in the presence of a base (pyridine, triethylamine). $R^{10}$ in compound 3 can be $R^7$ when $X^{2'}$ is $NH_2$ or must be a carboxylic acid protecting group like allyl-, β-trimethylsilylethyl-, tert-butyl- or 4-(trimethylsilyl)-2-buten-1-yl- or benzyl, when $X^{2'}$ is —OH. The carboxylic acid protecting group can be removed in the last step without cleavage of the internal amide or ester bond with such agents as Pd(0)/morpholine or Pd(0)/$Bu_3SnH$ for the allyl group, $Bu_4NF$ for the β-trimethylsilylethyl group, formic acid for the tert-butyl group or Pd(0) for the 4-(trimethylsilyl)-2-buten-1-yl group or catalytic hydrogenation for the benzyl group.

The acid 1, wherein the dotted line is absent and thus m is 1, used as starting material can be prepared in analogy to the examples given in EP 0116277 and EP 0115274. The acid 1, wherein the dotted line is present and forms a double bond are prepared as depicted in scheme 1a below. Starting from the ester of formula 1a which is transformed to the corresponding unsaturated compound 1b as depicted in scheme 1a:

SCHEME 1a

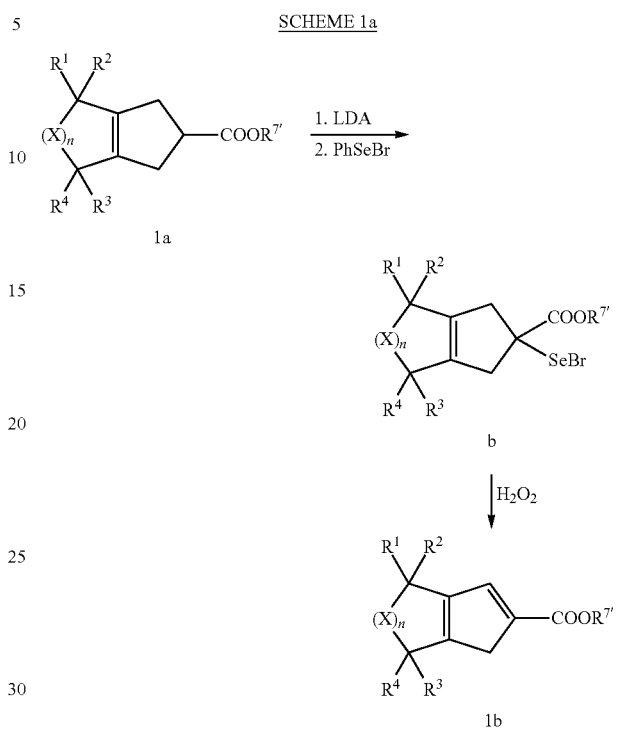

wherein the symbols are as defined above, $R^{7'}$ is alkyl, LDA is lithium diisopropylamide and Ph is phenyl.

Compounds of formula I, wherein Y is —CH=CH—, i.e. compounds of formula IB may be prepared according to scheme 2:

SCHEME 2

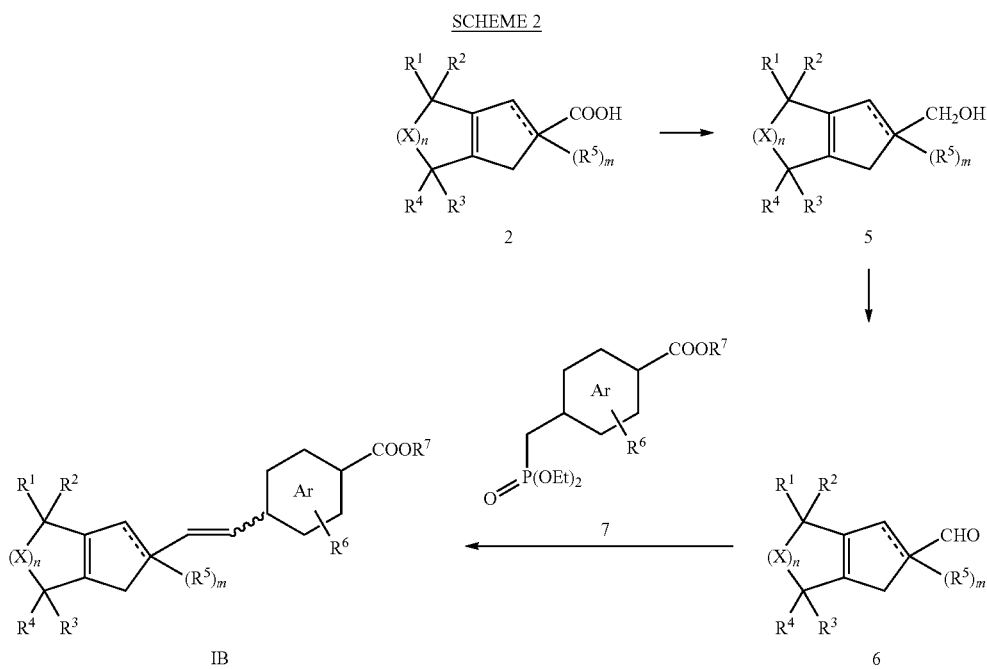

wherein the symbols are as defined above and Et signifies ethyl.

The acid 2 can be reduced to the alcohol 5 (e.g. with LiAlH$_4$, or a borane complex), oxidized to the aldehyde 6 by a Swern or a Dess-Martin oxidation or with pyridinium chlorochromate and then condensed in a Wittig-Horner reaction with a suitable phosphonate 7 using a strong base like NaH or lithium-bis-(trimethylsilyl)-amide (LiHMDS) to give the olefinic compounds of formula IB wherein R$^7$ is different from hydrogen and which can be hydrolyzed if desired to a compound of formula IB wherein R$^7$ is hydrogen. The double bond may be in a E/Z mixture, or preferably in the E configuration. The Wittig-Horner reaction is highly trans selective and Scheme 2 illustrates the synthesis of the trans isomer. The corresponding cis isomer may be prepared in accordance with Scheme 3, followed by Lindlar reduction of the triple bond.

Compounds of formula I wherein Y is an acetylenic group (—C≡C—), namely compounds of formula IC can be prepared according to scheme 3:

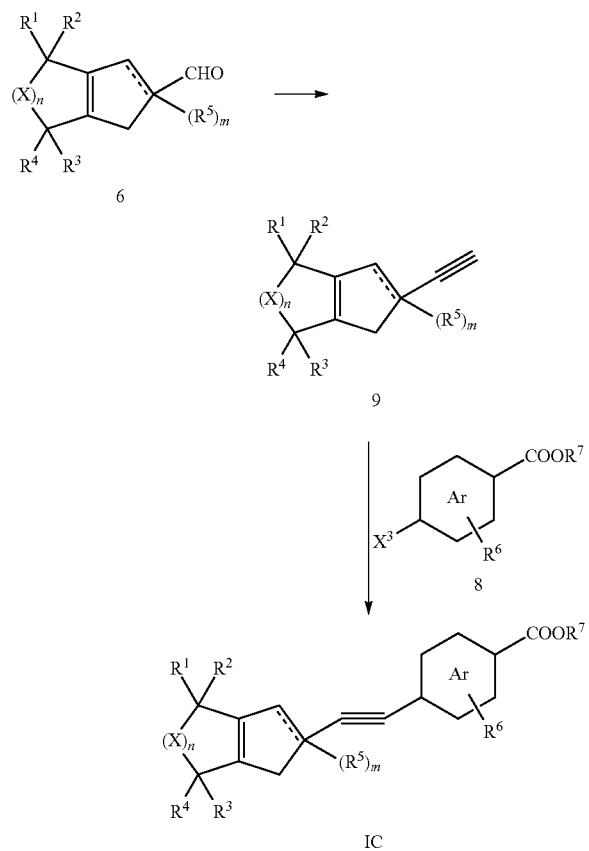

wherein the symbols are as defined above and X$^3$ is halogen, preferably bromine or iodine.

The aldehyde 6 can be transformed into the acetylenic derivative 9 according to the method of Corey and Fuchs by reaction with P(C$_6$H$_5$)$_3$/CBr$_4$ and subsequently with butyllithium. The lithiated product is then coupled with a bromo or iodo substituted aromatic ester 8 in a Pd(0) catalyzed reaction to give a compound of formula IC wherein R$^7$ is different from hydrogen and which can be hydrolyzed to the product wherein R$^7$ is hydrogen if desired.

Compounds of formula I wherein Y is —CH$_2$O—, —CH$_2$S— or —CH$_2$NR$^{10}$—, i.e. compounds of formula ID, wherein Z is —O—, —S— or —NH—, can be synthesized according to Scheme 4 by using an alcohol 5 as starting material.

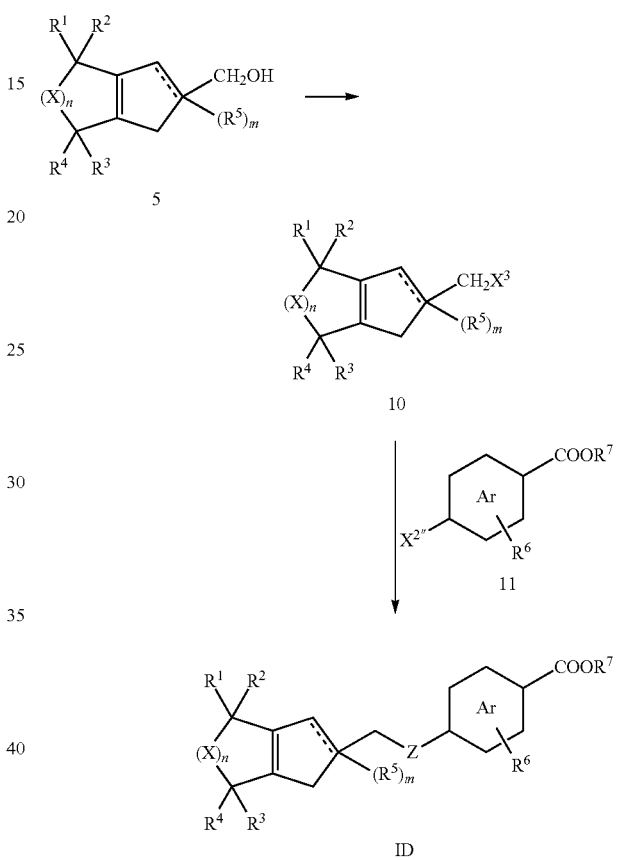

wherein the symbols are as defined above and X$^{2''}$ is —OH, —SH or —NH$_2$.

The hydroxy group of the alcohol 5 can be transformed to the halogenated derivative 10 with PX$_3^3$ or CX$_4^3$/(C$_6$H$_5$)$_3$P, wherein X$^3$ is a halogenide preferably a chloride or bromide, or to a sulfonate using mesyl chloride or tosyl chloride followed by reaction with compound 11 to give the product of formula ID, which may be hydrolyzed to the product of formula ID wherein R$^7$ is hydrogen.

Compounds of formula ID, wherein Z is sulfur can be oxidized to the sulfoxide or the sulfone with peroxides. An alternative method for the synthesis of compounds of formula ID wherein Z is oxygen or sulfur is according to Mitsunobu by reacting the alcohol 5 with compound 11 wherein X$^{2''}$ is OH or SH.

Compounds of formula I, wherein Y is —COCH═CH—, i.e. compounds of formula IE can be synthesized according to scheme 5.

SCHEME 5

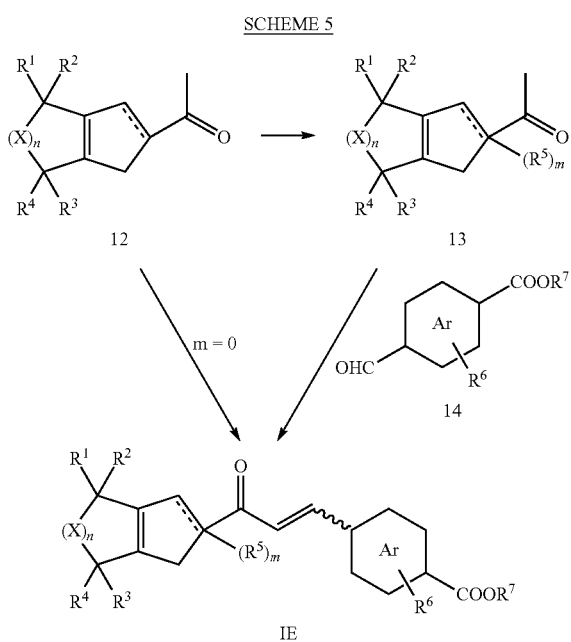

wherein the symbols are as defined above.

The ketone 12 can be alkylated at the higher substituted position by using sodium hydride (NaH), potassium hydride (KH) or potassium tert-butylate as a base to give compounds 13 wherein the dotted bond is absent and m is 1. Aldol condensation of compounds 12 or 13, respectively, with formyl compound 14 in the presence of catalytic amounts of sodium hydroxyde (NaOH), piperidine, piperidinium acetate or piperidinium tosylate yields compounds of formula IE wherein $R^7$ is different from hydrogen which can be transformed into the final product IE wherein $R^7$ is hydrogen by hydrolysis of the ester group.

Compound of formula I, wherein Y is —CHOHCH=CH—, i.e. compounds of formula IF can be prepared according to scheme 6 by reduction of a compound of formula IE with for example $NaBH_4$ or with $NaBH_4$/$CeCl_3$.

SCHEME 6

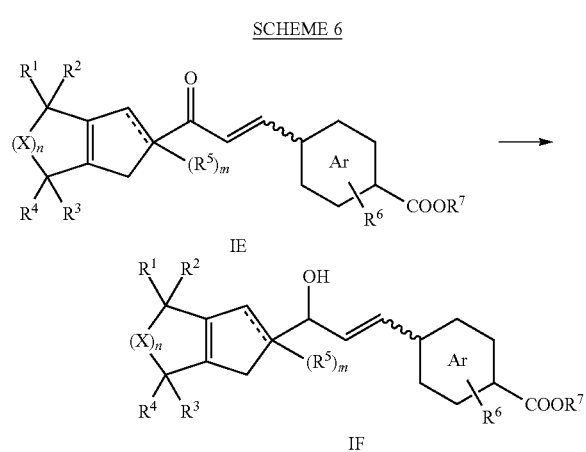

wherein the symbols are as defined above.

Compounds of formula IF wherein $R^7$ is different from hydrogen can be transformed into the product IF wherein $R^7$ is hydrogen by hydrolysis.

The compounds of formula I, wherein Y is —$NR^{10}CO$—, i.e. compounds of formula IG can be prepared according to scheme 7. Various methods are known for the transformation of acid 2 into amine 15 (Hofmann, Lossen, Curtius or Schmidt-rearrangement)

SCHEME 7

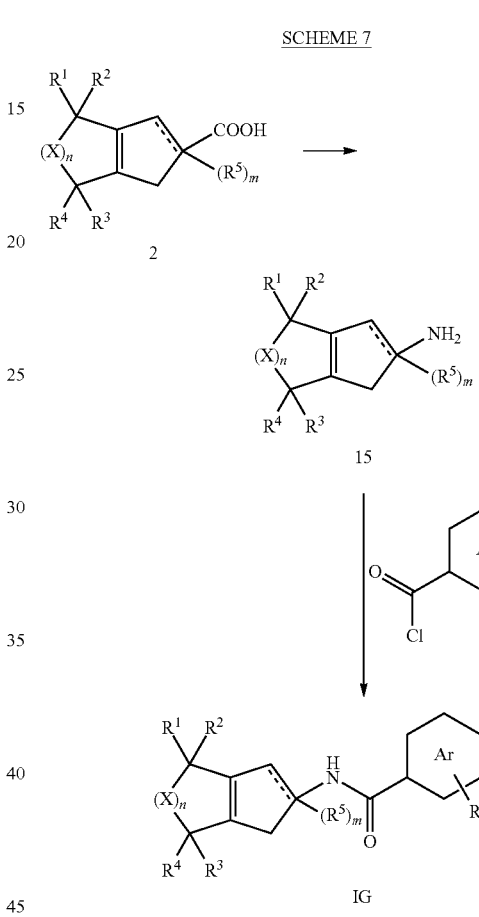

wherein the symbols are as defined above.

The amine 15 for example can be reacted with a terephthalic acid chloride derivative or a suitable acid chloride 16 in presence of pyridine or triethyl amine to give the amide of formula IG wherein $R^7$ is different from hydrogen. Hydrolysis of the ester group yields the product of formula IG wherein $R^7$ is hydrogen.

In the alternative the internal amide bond can also be formed by reaction of the amine 15 with terephthalic acid half ester and dicyclohexylcarbodiimide.

Compounds of formula I, wherein Y is —OCO—, i.e. compounds of formula IH can be synthesized according to scheme 8.

Compound 12 can be oxidized according to Baeyer-Villiger with a peroxyacid to give the hydroxy compound 17. Esterification is performed using known methods as for example by reaction of an acid chloride 16 and a base.

SCHEME 8

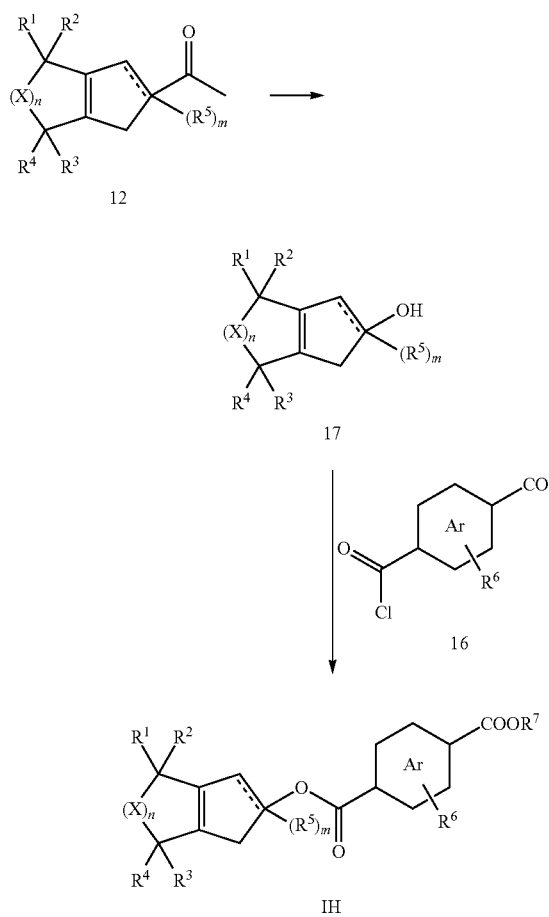

wherein the symbols are as defined above.

Compounds of formula I-2 can be prepared according to the method depicted in Scheme 9:

SCHEME 9

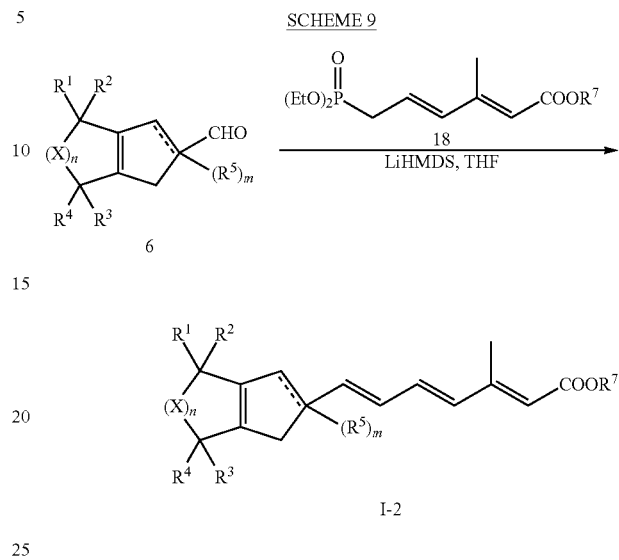

wherein the symbols are as defined above.

The aldehyde 6 is reacted with the phosphonate 18 in a Wittig-Horner reaction in presence of a strong base as for example sodium hydride or lithium-bis-(trimethylsilyl)-amide (LiHMDS) in an inert solvent as for example THF to the ester of formula I-2, wherein $R^7$ is alkyl. This ester may the subsequently be hydrolyzed to the compound of formula I-2, wherein $R^7$ is hydrogen.

Compounds of formula I, wherein $R^5$ is alkoxy, alkylthio and alkyl-$NR^{10}$— and Y is different from —OCO—, —NHCO—, —OCH$_2$—, —SCH$_2$—, —SOCH$_2$—, —SO$_2$CH$_2$— or —$NR^{10}$CH$_2$— can be prepared by known methods for example they may be prepared according to the methods depicted in scheme 10.

SCHEME 10

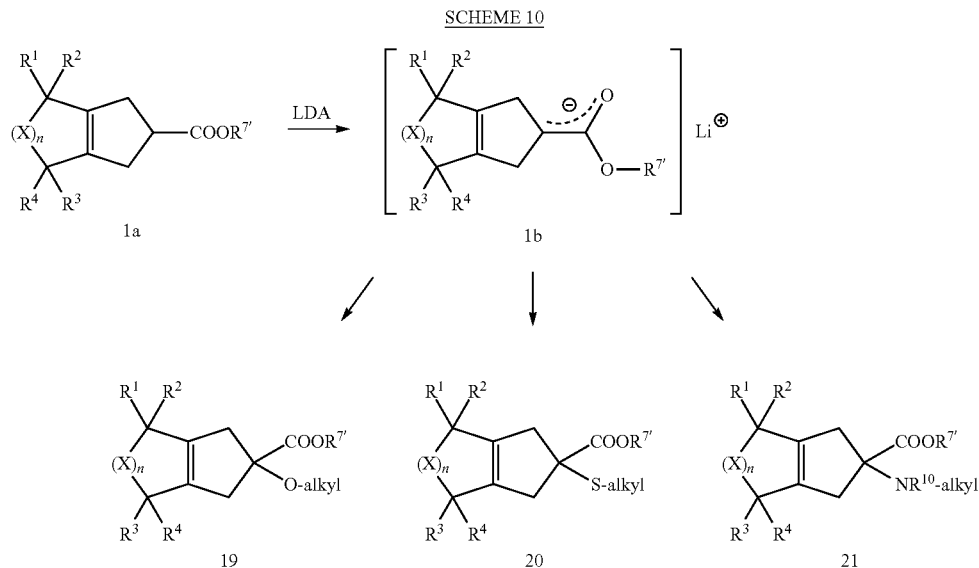

wherein the symbols are as defined above.

The ester 1a can be transformed into the ester enolate 1b in presence of a strong, non-nucleophilic base like lithium diisopropylamide; this enolate can then be reacted with:

a) MoO$_5$-complex to give the corresponding α-hydroxy compound which can then be alkylated with an alkylhalogenide (R$^5$X$^1$) to form compound 19 which is then transformed according to one of the reaction schemes above into the desired compound of formula I;

b) a suitable disulfide alkyl-S—S-alkyl to give the corresponding α-thioester 20;

c) a [NH$_2^\oplus$]-synthon (for a review of such synthons see G. Boche in Houben-Weyl, Methods of Organic Chemistry, Vol. E21e, p. 5133 (1995) or D. Enders et al. in Tetrahedron 1998, 54, 10069).

Compounds of formula IA, wherein Y is —OCH$_2$—, —SCH$_2$—, —SOCH$_2$—, —SO$_2$CH$_2$— or —NR$^{10}$CH$_2$— and R$^5$ is alkyl, alkoxy-alkyl-, alkenyl, alkynyl, benzyl, cycloalkyl-alkyl, phenyl-alkyl, can be prepared according to the method depicted in scheme 11:

In some embodiments, the RAR selective agonist is selective for RARβ or RARγ. A RAR selective agonist is selective for a target if it binds to the target with higher affinity compared to binding with another molecule, such as a different RAR. In exemplary embodiments, a RAR selective agonist is selective for RARβ over RARα and/or RARγ. In exemplary embodiments, a RAR selective agonist is selective for RARγ over RARα and/or RARβ. Thus, a RAR selective agonist tends to bind to a particular target with high binding affinity. In some embodiments, a high binding affinity is given by a dissociation constant K$_d$ of about 10$^{-7}$ M or less. In exemplary embodiments, a high binding affinity is given by a dissociation constant K$_d$ of about 10$^{-8}$ M or less, about 10$^{-9}$ M or less, about 10$^{-10}$ M or less, about 10$^{-11}$ M or less, about 10$^{-12}$ M or less, about 10$^{-13}$ M or less, about 10$^{-14}$ M or less or about 10$^{-15}$ M or less.

Protocols for making various compounds of the invention are described in U.S. Pat. No. 6,528,677 B1.

SCHEME 11

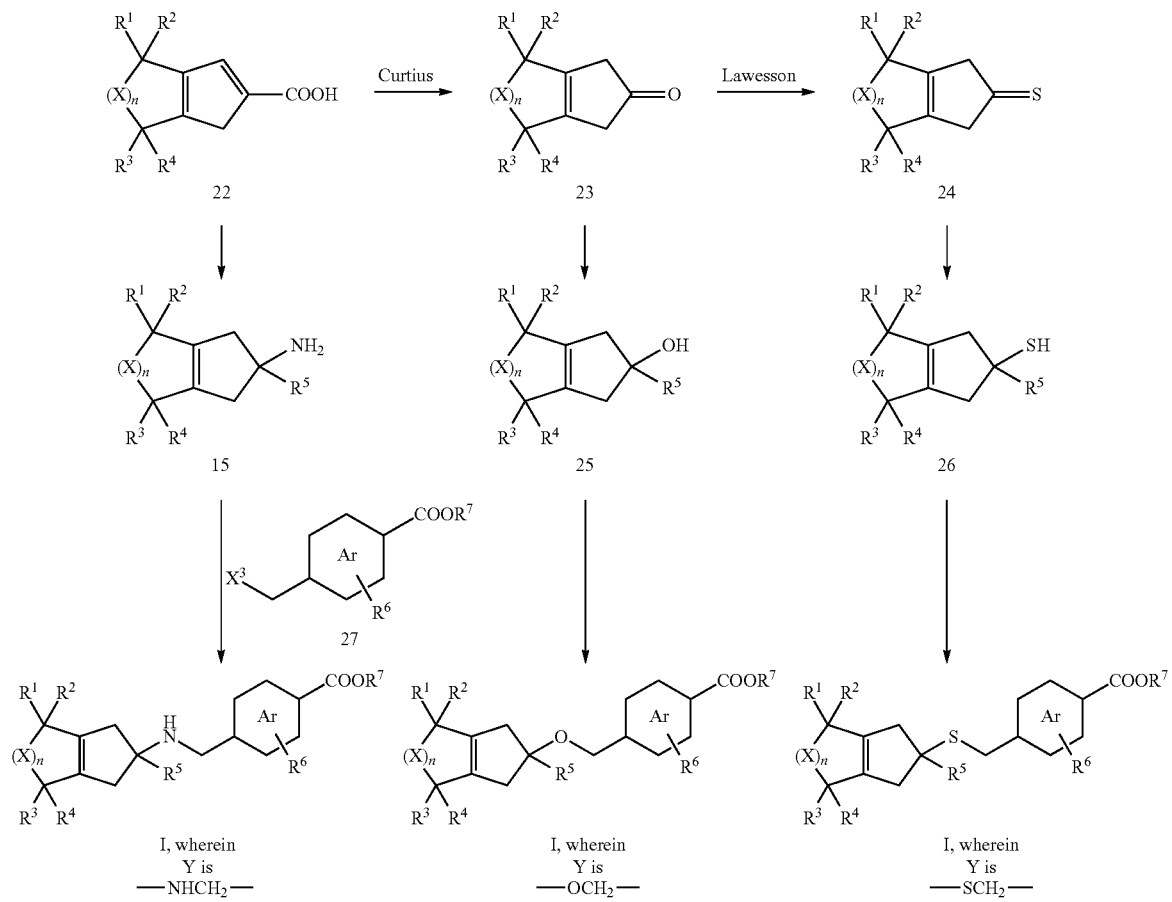

wherein the symbols are as defined above.

The acid 22, synthesis described in example 11, can be transformed in a Curtius reaction into the corresponding ketone 23 which will react with Lawesson reagent to the thioketone 24. Addition of a Grignard reagent will lead to compounds 25 and 26, respectively. Alkylation of compounds 15, 25 or 26 with bromomethyl derivative 27 will give the desired products of formula IA, wherein Y is —NHCH—, —OCH$_2$— or —SCH$_2$—.

Formulations

In one aspect, the invention provides formulations of an active agent such as a RAR selective agonist, with formulations for topical or oral administration being an exemplary mode of delivery. The formulations (sometimes referred herein to as a composition) typically comprise an active agent (or a pharmaceutically acceptable salt thereof) and a carrier medium.

An "active agent", "therapeutic agent" or "drug" refers to any compound that is effective in treating a targeted disorder, disease or condition or in inducing a medically beneficial effect. Exemplary active agents include a RAR selective agonist disclosed herein and a salt thereof.

A "carrier medium" or "carrier" refers to one or more excipients, diluents, carriers, additives and combinations thereof known in the art that may be combined with an active agent (such as a RAR selective agonist disclosed herein) to enhance, facilitate or enable the production, storage, administration, delivery or effectiveness of the active compound. For topical formulations, a carrier medium will be dermatologically acceptable, preferably designed to reduce or avoid undue toxicity, incompatibility, instability, allergic response and the like when applied to skin. For oral formulations, a carrier medium will be orally acceptable, preferably designed to reduce or avoid undue toxicity, incompatibility, instability, allergic response and the like when applied in the mouth.

Active agents in the formulations described herein should be present in a therapeutically effective amount. A "therapeutically effective amount" means the amount of a compound that, when administered to a mammal for treating or preventing a disease, is sufficient to effect such treatment or prevention of the disease or to induce a medically beneficial effect. The therapeutically effective amount will vary depending on the compound, the specific nature of the disease and its severity and the age, weight or other characteristic of the mammal to be treated. The dosage may be delivered in a conventional pharmaceutical composition by a single administration, by multiple applications, or via controlled release, as needed to achieve the most effective results. Dosing will continue for as long as is medically indicated, which depending on the severity of the disease may range from a few weeks to several months.

In some embodiments, the active agent will be present in an amount of not more than about a percentage selected from 10%, 5%, 2%, 1%, 0.1%, 0.05%, 0.02%, 0.01%, 0.005%, 0.002%, 0.001%, 0.0005%, 0.0002%, 0.0001%, 0.00005%, 0.00002% and 0.00001% by weight based on the total weight of the pharmaceutical formulation. In exemplary embodiments, a formulation comprises an active agent (e.g. RAR selective agonist) in amount that is about 0.005 wt %. In exemplary embodiments, a formulation comprises an active agent (e.g. RAR selective agonist) in amount that is about 0.01 wt %. In exemplary embodiments, a formulation comprises an active agent (e.g. RAR selective agonist) in amount that is about 0.05 wt %. In some embodiments, a formulation comprises an active agent (e.g. RAR selective agonist) in an amount that is about 0.005 wt % to about 0.05 wt %, preferably about 0.005 wt % to about 0.01 wt % or preferably about 0.01 wt % to about 0.05 wt %. In some embodiments, a formulation comprises an active agent (e.g. RAR selective agonist) in an amount that is about 0.00001 wt % to about 1 wt %. In exemplary embodiments, the dosage will range between about 0.005 and 0.05% active dose per component per application, preferably from about 0.005 to about 0.05% of active dose. In non-limiting embodiments, for example, a formulation comprises an active agent (e.g. RAR selective agonist) in an amount that is or is at least about a weight percentage (wt %) selected from 0.00001%, 0.00002%, 0.00003%, 0.00004%, 0.00005%, 0.00006%, 0.00007%, 0.00008%, 0.00009%, 0.0001%, 0.0002%, 0.0003%, 0.0004%, 0.0005%, 0.0006%, 0.0007%, 0.0008%, 0.0009%, 0.0010%, 0.0020%, 0.0030%, 0.0040%, 0.0050%, 0.0060%, 0.0070%, 0.0080%, 0.0090%, 0.0100%, 0.0110%, 0.0120%, 0.0130%, 0.0140%, 0.0150%, 0.0160%, 0.0170%, 0.0180%, 0.0190%, 0.0200%, 0.0210%, 0.0220%, 0.0230%, 0.0240%, 0.0250%, 0.0260%, 0.0270%, 0.0280%, 0.0290%, 0.0300%, 0.0310%, 0.0320%, 0.0330%, 0.0340%, 0.0350%, 0.0360%, 0.0370%, 0.0380%, 0.0390%, 0.0400%, 0.0410%, 0.0420%, 0.0430%, 0.0440%, 0.0450%, 0.0460%, 0.0470%, 0.0480%, 0.0490%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9% and 5.0%. Ranges incorporating any of these and other values disclosed herein as endpoints may also be suitable.

The term "about" when used to qualify a percentage or amount of a component herein can be interpreted to allow for minor adjustments in the value of the percentage or amount while maintaining the functionality of the component in the overall formulation. In some embodiments, the term "about" when used to qualify a percentage herein refers to a value that falls in a range, inclusive of the endpoints, that is 5% above or below the value of the percentage. Thus, in some embodiments, about 1% refers to a value in the range of 0.95% to 1.05% and about 2% refers to a value in the range of 1.9% to 2.1%. In some embodiments, the term "about" when used to qualify a percentage herein refers to the value of the percentage itself. Thus, in some embodiments, about 1% refers to 1%.

In some embodiments, the methods disclosed herein also include systemic administration of RAR agonists in simultaneous or sequential combination with a further active agent or drug. Thus, in some embodiments, a formulation further comprises an active agent or a drug in addition to a RAR selective agonist, i.e., the formulation further comprises a second active agent or a second drug.

Second active agents that can be used with the present invention include all drugs which can be delivered onto or through the skin for either a local or systemic effect, among others. These compounds include agents in all of the major therapeutic areas, including, but not limited to, ACE inhibitors, adenohypophoseal hormones, adrenergic neuron blocking agents, adrenocortical steroids, inhibitors of the biosynthesis of adrenocortical steroids, alphaadrenergic agonists, alpha-adrenergic antagonists, selective alpha-two-adrenergic agonists, analgesics, antipyretics and anti-inflammatory agents, androgens, local and general anesthetics, antiaddictive agents, antiandrogens, antiarrhythmic agents, antiasthmatic agents, anticholinergic agents, anticholinesterase agents, anticoagulants, antidiabetic agents, antidiarrheal agents, antidiuretic, antiemetic and prokinetic agents, antiepileptic agents, antiestrogens, antifungal agents (e.g., amphotericin B, clotrimazole, nystatin, ketoconazole, miconazole, butocouazole, haloprogin, etc.), antihypertensive agents, anti-inflammatory agents (e.g., steroidal compounds such as dexamethasone, betamethasone, prednisone, prednisolone, triamcinolone, hydrocortisone, alclometasone, amcinonide, diflorasone, etc. as well as non-steroidal anti-inflammatories), anti-itch and irritation-reducing compounds (e.g., antihistamines such as diphenhydramine and psoriasis treatments), antimicrobial agents, antimigraine agents, antimuscarinic agents, antineoplastic agents, antiparasitic agents (e.g., lindane, anthralin, etc.), antiparkinson's agents, antiplatelet agents, antiprogestins, anticeptic agents (e.g., povidone-iodine, methylbenzethonium chloride, etc.), antithyroid agents, antitussives, antiviral agents (e.g., acyclovir and idoxuridine, etc.), atypical antidepressants, azaspirodecanediones, barbituates, benzodiazepines, benzothiadiazides, beta-adrenergic agonists, beta-adrenergic antagonists, selective beta-one-adrenergic antagonists, selective beta-two-adrenergic agonists, bile salts, burn relievers (e.g., o-amino-ptoluenesulfonamide, monoacetate, etc.), agents affecting volume and composition of body fluids, butyrophenones, agents affecting calcification, calcium channel blockers, cardiovascular drugs, catecholamines and sympathomimetic drugs, cholinergic agonists, cholinesterase reactivators, depigmenting agents (e.g., monobenzone), dermatological agents, diphenylbutylpiperidines, diuretics, ergot alkaloids, ganglionic blocking agents, ganglionic stimulating agents, hydantoins, agents for control of gastric acidity and treatment of peptic ulcers, hematopoietic agents, histamines, histamine antagonists, hormonal agents (e.g., estrogens, oestriol), 5-hydroxytryptamine antagonists, drugs for the treatment of hyperlipoproteinemia, hypnotics and sedatives, immunosuppressive agents, laxatives, methylxanthines, monoamine oxidase inhibitors, neuromuscular blocking agents, organic nitrates, pancreatic enzymes, phenothiazines, progestins, prostaglandins, agents for the treatment of psychiatric disorders, retinoids, sodium channel blockers, agents for spasticity and acute muscle spasms, succinimides, thioxanthines, thrombolytic agents, thyroid agents, tricyclic antidepressants, inhibitors of tubular transport of organic compounds, drugs affecting uterine motility, vasodilators, vitamins and the like.

Representative drugs include, for example, bepridil, diltiazem, felodipine, isradipine, nicardipine, nifedipine, nimodipine, nitredipine, verapamil, dobutamine, isoproterenol, carterolol, labetalol, levobunolol, nadolol, penbutolol, pindolol, propranolol, sotalol, timolol, acebutolol, atenolol, betaxolol, esmolol, metoprolol, albuterol, bitolterol, isoetharine, metaproterenol, pirbuterol, ritodrine, terbutaline, alclometasone, aldosterone, amcinonide, beclomethasone, dipropionate, betamethasone, clobetasol, clocortolone, cortisol, cortisone, corticosterone, desonide, desoximetasone, 11-desoxycorticosterone, 11-desoxycortisol, dexamethasone, diflorasone, fludrocortisone, flunisolide, fluocinolone, fluocinonide, fluorometholone, flurandrenolide, halcinonide, hydrocortisone, medrysone, 6.alpha.-methylprednisolone, mometasone, paramethasone, prednisolone, prednisone, tetrahydrocortisol, triamcinolone, benoxinate, benzocaine, bupivacaine, chloroprocaine, cocaine, dibucaine, dyclonine, etidocaine, lidocaine, mepivacaine, pramoxine, prilocaine, procaine, proparacaine, tetracaine, alfentanil, chloroform, clonidine, cyclopropane, desflurane, diethyl ether, droperidol, enflurane, etomidate, halothane, isoflurane, ketamine hydrochloride, meperidine, methohexital, methoxyflurane, morphine, propofol, sevoflurane, thiamylal, thiopental, acetaminophen, allopurinol, apazone, aspirin, auranofin, aurothioglucose, colchicine, diclofenac, diflunisal, etodolac, fenoprofen, flurbiprofen, gold sodium thiomalate, ibuprofen, indomethacin, ketoprofen, meclofenamate, mefenamic acid, meselamine, methyl salicylate, nabumetone, naproxen, oxyphenbutazone, phenacetin, phenylbutazone, piroxicam, salicylamide, salicylate, salicylic acid, salsalate, sulfasalazine, sulindac, tolmetin, acetophenazine, chlorpromazine, fluphenazine, mesoridazine, perphenazine, thioridazine, trifluorperazine, triflupromazine, disopyramide, encamide, flecamide, indecamide, mexiletine, moricizine, phenyloin, procainamide, propafenone, quinidine, tocamide, cisapride, domperidone, dronabinol, haloperidol, metoclopramide, nabilone, prochlorperazine, promethazine, thiethylperazine, trimethobenzamide, buprenorphine, butorphanol, dezocine, diphenoxylate, drocode, hydrocodone, hydromorphone, levallorphan, levorphanol, loperamide, meptazinol, methadone, nalbuphine, nalmefene, nalorphine, naloxone, naltrexone, oxybutynin, pentazocine, isosorbide dinitrate, nitroglycerin, theophylline, phenylephrine, ephidrine, pilocarpine, furosemide, tetracycline, chlorpheniramine, ketorolac, bromocriptine, guanabenz, prazosin, doxazosin, and flufenamid acid.

Still other representative drugs include benzodiazepines, such as alprazolam, brotizolam, chlordiazepoxide, clobazam, clonazepam, clorazepate, demoxepam, diazepam, flumazenil, flurazepam, halazepam, lorazepam, midazolam, nitrazepam, nordazepam, oxazepam, prazepam, quazepam, temazepam, triazolam, and the like; an antimuscarinic agent such as anisotropine, atropine, clidinium, cyclopentolate, dicyclomine, flavoxate, glycopyrrolate, hexocyclium, homatropine, ipratropium, isopropamide, mepenzolate, methantheline, oxyphencyclimine, pirenzepine, propantheline, scopolamine, telenzepine, tridihexethyl, tropicamide, and the like; an estrogen such as chlorotrianisene, siethylstilbestrol, methyl estradiol, estrone, estrone sodium sulfate, estropipate, mestranol, quinestrol, sodium equilin sulfate, 17β-estradiol (or estradiol), semi-synthetic estrogen derivatives such as the esters of natural estrogen, such as estradiol-17β-enanthate, estradiol-17β-valerate, estradiol-3-benzoate, estradiol-17β-undecenoate, estradiol 16,17-hemisuccinate or estradiol-17β-cypionate, and the 17-alkylated estrogens, such as ethinyl estradiol, ethinyl estradiol-3 isopropylsulphonate, and the like; an androgen such as danazol, fluoxymesterone, methandrostenolone, methyltestosterone, nandrolone decanoate, nandrolone phenpropionate, oxandrolone, oxymetholone, stanozolol, testolactone, testosterone, testosterone cypionate, testosterone enanthate, testosterone propionate, and the like; or a progestin such as ethynodiol diacetate, gestodene, hydroxyprogesterone caproate, levonorgestrel, medroxyprogesterone acetate, megestrol acetate, norethindrone, norethindrone acetate, norethynodrel, norgestrel, progesterone, and the like.

In some embodiments, the second active agent is an antibiotic. Thus, in some embodiments, the formulation further comprises an antibiotic. As used herein, an "antibiotic" refers to any compound having activity against either Gram-positive or Gram-negative organisms (i.e., inhibits the growth or destroys the development of either Gram-positive or Gram-negative organisms). Stedman's Medical Dictionary, Illustrated, (25th Ed.), Williams & Wilkins: Baltimore (1990) and Mosby's Medical, Nursing, & Allied Health Dictionary, (5th Ed.), Mosby: St. Louis (1998).

Any suitable antibiotic can be employed provided that the antibiotic remains stable in the formulation. Preferably, the stability is over a prolonged period of time, e.g., up to about 3 years, up to about 1 year, or up to about 6 months, typically experienced in the manufacturing, packaging, shipping, and/or storage of the composition. Suitable antibiotics are disclosed, e.g., in Physician's Desk. Reference (PDR), Medical Economics Company (Montvale, N.J.), (53rd Ed.), 1999; Mayo Medical Center Formulary, Unabridged Version, Mayo Clinic (Rochester, Minn.), January 1998; Merck Index, An Encyclopedia of Chemicals, Drugs, and Biologicals, (11th Ed.), Merck & Co., Inc. (Rahway, N.J.), 1989; and references cited therein. Other topically-active compounds are listed in Remington's Pharmaceutical Sciences, 17th Ed., Merck Publishing Co., Easton, Pa. (1985).

Suitable classes of antibiotic include, e.g., β-lactams, aminoglycosides, antifungal agents, and combinations thereof. Suitable antibiotics include, e.g., cilastatin, clavulanic acid, folinic acid, probenecid, pyridoxine, sulbactam, dapsone, ethambutol, isoniazid, pyrazinamide, rifampin, streptomycin, capreomycin, ethionamide, para aminosalicylic acid, cycloserine, ciprofloxacin, nalidixic acid, norfloxacin, ofloxacin, imipenam, meropenem, cilistatin, cefadroxil, cefazolin, cephalexin, cephalothin, cefaclor, cefamandole, cefonicid, cefoxitin, cefuroxine, cefoperazone, cefotaxime, ceftazidime, ceftizoxime, ceftriaxone, moxalactam, cefepine, bacitracin, vancomycin, aztreonam, amoxicillin, clavulanic acid, benzathine, penicillin g, penicillin v, ampicillin, carbenicillin. indamyl, carbenicillin, mezlocillin, piperacillin, ticarcillin, cloxacillin, dicloxacillin, floxacillin, methicillin, nafcillin, oxacillin, colistmethate, polyrnixin b, trimethoprim, cotrimoxazole, mafenide, sulfadiazine, sodium sulfacetamide, sulfacytine, sulfadiazine, sulfamethoxazole, sulfapyridine, sulfasalazine, sulfisoxazole, chloramphenicol, clindamycin, spectinomycin, azithromycin, clarithromycin, erythrmoycin, erythromycin estolate, spiramycin, chlortetracycline, demeclocycline, doxycycline, minocycline, oxytetracycline, amikacin, kanamycin, neomycin, streptomycin, tobramycin, nitrofurantoin, griseofulvin, potassium iodide, fluconazole, itraconazole, ketoconazole, miconazole, clotrimazole, amphotericin b, nystatin, niclosamide, nifurtimox, piperazine, praziquantel, pyrantel pamoate, ascariasis, pinworm, thiabendazole, amodiaquine, chloroquine, hydroxychloroquine, mefloquine, primaquine, pyrimethamine, quinidine gluconate, fansidar, diloxanide furoate, melarsoprol, nifurtimox, paromomycin, pentamidine, sodium stibogluconate, suramin, metronidazole, foscarnet, 3-deoxythmidin-2-ene, dideoxycytosine, dideoxyinosine, lamivudine, azidothymidine, indinavir, ritonavir, saquinavir, acyclovir, idoxuridine, ribavirin, vidarabine, amantidine, rinantidine, pharmaceutically acceptable salts thereof, and combinations thereof.

Specifically, the antibiotic can be at least one of amphomycin, apramycin, avilamycin, azithromycin, bacitracin, bactiracin zinc, clarithromycin, clindamycin, clindamycin hydrochloride, clindamycin palmitate hydrochloride, clindamycin phosphate, dirithromycin, erythromycin, erythromycin acistrate, erthromycin estolate, erthryomycin ethlylsuccinate, erthryomycin gluceptate, erythromycin lactobionate, erthromycin propionate, erthromycin stearate, fosfomycin, fosfomycin tromethamine, josamycin, kitasamycin, lexithromycin, lincomycin, limcomycin hydrochloride, metronidazole hydrochloride, metronidazole phosphate, mirincamycin hydrochloride, paldimycin, paulomycin, pirlimycin hydrochloride, ranimycin, relomycin, roxithromycin, spectinomycin hydrochloride, spiramycin, stallimycin hydrochloride, tobramycin, vancomycin, vancomycin hydrochloride, zorbamycin, mupirocin, mupirocin calcium, and parachlorophenol.

In some embodiments, the second active agent is an analgesic. Thus, in some embodiments, a formulation further comprises an analgesic. An analgesic is an agent that is capable of reducing or eliminating pain. Various classes of analgesics include nonsteroidal anti-inflammatory drugs (NSAIDs) (e.g., salicylates, propionic acid derivatives, acetic acid derivatives, enolic acid derivatives, fenamic acid derivatives, COX-2 inhibitors, sulphonanilides, etc.) and opiates (e.g., morphine, codeine, thebaine, papverine, etc.). Exemplary analgesics include acetaminophen; alfentanil hydrochloride; aminobenzoate potassium; aminobenzoate sodium; anidoxime; anileridine; anileridine hydrochloride; anilopam hydrochloride; anirolac; antipyrine; aspirin; benoxaprofen; benzydamine hydrochloride; bicifadine hydrochloride; brifentanil hydrochloride; bromadoline maleate; bromfenac sodium; buprenorphine hydrochloride; butacetin; butixirate; butorphanol; butorphanol tartrate; carbamazepine; carbaspirin calcium; carbiphene hydrochloride; carfentanil citrate; ciprefadol succinate; ciramadol; ciramadol hydrochloride; clonixeril; clonixin; codeine; codeine phosphate; codeine sulfate; conorphone hydrochloride; cyclazocine; dexoxadrol hydrochloride; dexpemedolac; dezocine; diflunisal; dihydrocodeine bitartrate; dimefadane; dipyrone; doxpicomine hydrochloride; drinidene; enadoline hydrochloride; epirizole; ergotamine tartrate; ethoxazene hydrochloride; etofenamate; eugenol; fenoprofen; fenoprofen calcium; fentanyl citrate; floctafenine; flufenisal; flunixin; flunixin meglumine; flupirtine maleate; fluproquazone; fluradoline hydrochloride; flurbiprofen; hydromorphone hydrochloride; ibufenac; indoprofen; ketazocine; ketorfanol; ketorolac tromethamine; letimide hydrochloride; levomethadyl acetate; levomethadyl acetate hydrochloride; levonantradol hydrochloride; levorphanol tartrate; lofemizole hydrochloride; lofentanil oxalate; lorcinadol; lornoxicam; magnesium salicylate; mefenamic acid; menabitan hydrochloride; meperidine hydrochloride; meptazinol hydrochloride; methadone hydrochloride; methadyl acetate; methopholine; methotrimeprazine; metkephamid acetate; mimbane hydrochloride; mirfentanil hydrochloride; molinazone; morphine sulfate; moxazocine; nabitan hydrochloride; nalbuphine hydrochloride; nalmexone hydrochloride; namoxyrate; nantradol hydrochloride; naproxen; naproxen sodium; naproxol; nefopam hydrochloride; nexeridine hydrochloride; noracymethadol hydrochloride; ocfentanil hydrochloride; octazamide; olvanil; oxetorone fumarate; oxycodone; oxycodone hydrochloride; oxycodone terephthalate; oxymorphone hydrochloride; pemedolac; pentamorphone; pentazocine; pentazocine hydrochloride; pentazocine lactate; phenazopyridine hydrochloride; phenyramidol hydrochloride; picenadol hydrochloride; pinadoline; pirfenidone; piroxicam olamine; pravadoline maleate; prodilidine hydrochloride; profadol hydrochloride; propiram fumarate; propoxyphene hydrochloride; propoxyphene napsylate; proxazole; proxazole citrate; proxorphan tartrate; pyrroliphene hydrochloride; remifentanil hydrochloride; salcolex; salicylamide; salicylate meglumine; salsalate; sodium salicylate; spiradoline mesylate; sufentanil; sufentanil citrate; talmetacin; talniflumate; talosalate; tazadolene succinate; tebufelone; tetrydamine; tifurac sodium; tilidine hydrochloride; tiopinac; tonazocine mesylate; tramadol hydrochloride; trefentanil hydrochloride; trolamine; veradoline hydrochloride; verilopam hydrochloride; volazocine; xorphanol mesylate; xylazine hydrochloride; zomepirac sodium; and zucapsaicin. Other pharmaceutically acceptable forms, such as alternative pharmaceutical salts, of these and other known analgesics may also be combined with a RAR selective agonist disclosed herein.

In some embodiments, the second active agent is an anesthetic. Thus, in some embodiments, a formulation further comprises an anesthetic. An anesthetic is an agent that reversibly depresses neuronal function, producing total or partial loss of sensation. Exemplary anesthetics include aliflurane; articaine; benoxinate hydrochloride; benzocaine; biphenamine hydrochloride; bupivacaine hydrochloride; butamben; butamben picrate; chloroprocaine hydrochloride; cocaine; cocaine hydrochloride; cyclopropane; desflurane; dexivacaine; diamocaine cyclamate; dibucaine; dibucaine hydrochloride; dyclonine hydrochloride; enflurane; ether; ethyl chloride; etidocaine; etoxadrol hydrochloride; euprocin hydrochloride; fluoroxene; halothane; isobutamben; isoflurane; ketamine hydrochloride; levobupivacaine; levoxadrol hydrochloride; lidocaine; lidocaine hydrochloride; mepivacaine hydrochloride; methohexital sodium; methoxyflurane; midazolam hydrochloride; midazolam maleate; minaxolone; norflurane; octodrine; oxethazaine; phencyclidine hydrochloride; pramoxine hydrochloride; prilocaine hydrochloride; procaine hydrochloride; propanidid; proparacaine hydrochloride; propofol; propoxycaine hydrochloride; pyrrocaine; risocaine; rodocaine; roflurane; ropivacaine; salicyl alcohol; sevoflurane; teflurane; tetracaine; tetracaine hydrochloride; thiamylal; thiamylal sodium; thiopental sodium; tiletamine hydrochloride; and zolamine hydrochloride. Other pharmaceutically acceptable forms, such as alternative pharmaceutical salts, of these and other known anesthetics may also be combined with a RAR selective agonist disclosed herein.

The compounds that can be used in the present invention, including the compounds listed above, are meant to include all pharmaceutically acceptable salts and conjugates.

Topical Administration

In one aspect, the invention provides a formulation comprising an active agent, such as a RAR selective agonist, and a carrier medium, wherein the formulation is suitable for topical administration. "Topical administration" means the application or spreading of a composition onto the surface of keratinous tissue. Keratinous tissue includes keratin-containing layers disposed as the outermost protective covering of mammals and includes, but is not limited to, skin, hair and nails. A "topical formulation" includes compositions suitable for topical administration on keratinous tissue. Such compositions are typically dermatologically-acceptable in that they do not have undue toxicity, incompatibility, instability, allergic response and the like, when applied to skin. Topical formulations of the present invention can have a selected viscosity to avoid significant dripping or pooling after application to skin.

An active agent may also be formulated for transdermal delivery. The term "transdermal delivery" refers to the diffusion of an agent across the barrier of the skin, nail, hair, claw or hoof resulting from topical administration or other application of a formulation. The stratum corneum acts as a barrier and few pharmaceutical agents are able to penetrate intact skin. In contrast, the epidermis and dermis are permeable to many solutes and absorption of drugs therefore occurs more readily through skin, nail, hair, claw or hoof that is abraded or otherwise stripped of the stratum corneum to expose the epidermis. Transdermal delivery includes injection or other delivery through any portion of the skin, nail, hair, claw or hoof or mucous membrane and absorption.

The formulations of the present invention can be incorporated into all types of vehicles. Non-limiting examples of suitable vehicles include liquids, emulsions (e.g., water-in-oil, water-in-oil-in-water, oil-in-water, oil-in-water-in-oil, oil-in-water-in-silicone emulsions), creams, lotions, solutions (both aqueous and hydro-alcoholic), anhydrous bases (such as lipsticks and powders), gels, ointments and any combination of the forgoing as would be known to one of ordinary skill in the art. See for example, Remington's Pharmaceutical Sciences (Mack Pub. Co. 1995). The formulations of the present invention can also be used in many products including, but not limited to, sunscreen products, sunless skin tanning products, hair products, finger nail products, moisturizing creams, skin benefit creams and lotions, softeners, day lotions, foundations, night creams, lipsticks, cleansers, toners, masks, or other known applications. Additionally, the products can be formulated as leave-on or rinse-off products. In some embodiments, the formulations can be oil-free, substantially anhydrous, and/or anhydrous. In some embodiments, the formulations comprise water. Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes that precipitate from the finished product.

In exemplary embodiments, an active agent such as a RAR selective agonist is in the form of a cream, ointment or gel. Such forms are particularly useful for topical administration. In the context of the present invention, an ointment includes any chemically suitable cream known in the art of retinoid agonists as applicable for administration to a subject. Examples of conventional ointment known in the art include the lipophilic ointment dispersed in a hydrophilic phase. For intranasal administration, useful forms include a nasal emulsion.

A lotion or cream may include a relatively large aqueous phase and a relatively small oil phase. Furthermore, the lotions and creams of the invention may include the active compound "all-in-solution" in the oil phase so that substantially none of the active compound crystallizes out at room temperature. In one embodiment, the lotion or cream may comprise a biphasic system, that is, a system wherein a portion (from about 30 to about 75% by weight) of the active compound is in solution in the oil phase and the remainder is in suspension in the aqueous phase.

Gel formulations can also be used in connection with the present invention. As will be appreciated by the skilled practitioner, gels are semisolid. Single-phase gels contain organic macromolecules distributed substantially uniformly throughout the carrier liquid, which is typically aqueous, but also may be a solvent or solvent blend. In various embodiments, conventional gelling agents can be used. In an exemplary embodiment, cellulose or its derivatives are used. In an exemplary embodiment, hydroxypropyl methyl cellulose, such as Methocel E4M, is used. Other gelling agents include methyl cellulose, hydroxypropyl cellulose, hydroxypropyl methyl cellulose, cellulose acetate, ethyl cellulose, methyl hydroxy ethyl cellulose, hydroxy ethyl cellulose and cellulose gum. Cellulose based gelling agents, particularly hydroxymethylcellulose and hydroxypropyl methyl cellulose, are also useful in some embodiments. In some embodiments, cross-linked acrylic polymers including Carbopol may be used.

In one embodiment, the formulation of the invention is viscous enough to form a firm gel. In one embodiment, the viscosity is in the range of 25,000-300,000 cps (centipoise) or 75,000-200,000 cps, based on Brookfield (LV) analysis.

Ointments, which are semisolid preparations, are typically, though not always, based on petrolatum or other petroleum derivatives. The specific ointment base to be used is typically one that provides for optimum delivery for the active agent chosen for a given formulation and preferably provides for other desired characteristics as well, e.g., emolliency or the like. As with other carriers or vehicles, an ointment base should be inert, stable, nonirritating and non-sensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Examples of oleaginous ointment bases include White Ointment USP, Yellow Ointment NF, Oleic Acid USP, Olive Oil USP, Paraffin USP, Petrolatum NF, White Petrolatum USP, Spermaceti Wax USP, Synthetic Spermaceti NF, Starch Glycerite NF, White Wax USP, and Yellow Wax USP. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight. See Remington: The Science and Practice of Pharmacy, supra, for further information.

Liquid formulations for topical administration may contain as excipients sterile water or saline, alkylene glycols such as propylene glycol, polyalkylene glycols such as polyethylene glycol, oils of vegetable origin, hydrogenated naphthalenes and the like. They may employ slightly acidic buffers in pH ranges of about 4 to about 6. Suitable buffers include acetate, ascorbate and citrate at concentrations ranging from about 5 mM to about 50 mM.

Any conventional carrier medium can be employed in the vehicles described herein. The carrier medium can be any organic or inorganic carrier material, such as water, gelatin, gum arabic, lactose, starch, magnesium stearate, talc, polyalkylene glycols, petroleum jelly and the like, sorbic acid and corn oil. A carrier medium suitable for use in a pharmaceutical formulation according to the present invention may be selected from the group consisting of one or more glycerides, such as, for example, one or more glycerol esters of saturated fatty acids or one or more polyglycolysed glycerides, cocoa butter, theobroma or the like, one or more high molecular weight polyethylene glycol, one or more polyoxyethylene, lanolin and derivatives thereof, one or more fatty acids, fatty alcohols, fatty esters (including, for example, caprylic acid, caprylic triglyceride or the like), and one or more organic oil (including, for example, hydrogenated vegetable oils) or the like.

The CTFA International Cosmetic Ingredient Dictionary and Handbook (2004 and 2008) describes a wide variety of non-limiting ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. aloe vera, chamomile, cucumber extract, *ginkgo biloba*, ginseng, and rosemary), anti-microbial agents, anti-oxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and manitol), exfoliants, water-proofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate). Other additional ingredients include one or more penetration enhancers (which may be surfactants, alcohols, esters, glycols or the like or any other suitable penetration enhancer), surfactants (which may be cationic, non-ionic, anionic or polymeric), emulsifiers, clays, anti-foaming agents, spreading agents, barriers, solubilizing agents for the therapeutic agent and the like.

Non-limiting examples of some of these ingredients are provided in the following subsections.

a. UV Absorption Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl pmethoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidenecamphor, and isopentyl 4-methoxycinnamate. Non-limiting examples of physical sunblocks include, kaolin, talc, petrolatum and metal oxides (e.g., titanium dioxide and zinc oxide). Compositions of the present invention can have UVA and UVB absorption properties. The compositions can have an sun protection factor (SPF) of 2, 3, 4, 5, 6, 7, 8, 9, 10, 11, 12, 13, 14, 15, 20, 25, 30, 35, 40, 45, 50, 55, 60, 70, 80, 90 or more, or any integer therein.

In some embodiments, a formulation comprises a UV absorption agent in an amount of about 0.05 to about 15 wt %, preferably from about 0.5 to about 5.0 wt %.

b. Moisturizing Agents

Non-limiting examples of moisturizing agents that can be used with the formulations of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, aloe barbadensis, aloe-barbadensis extract, aloe barbadensis gel, althea officinalis extract, apricot (*prunus armeniaca*) kernel oil, arginine, arginine aspartate, arnica montana extract, aspartic acid, avocado (*persea gratissima*) oil, barrier sphingolipids, butyl alcohol, beeswax, behenyl alcohol, beta-sitosterol, birch (*betula alba*) bark extract, borage (*borago officinalis*) extract, butcherbroom (*ruscus aculeatus*) extract, butylene glycol, *calendula officinalis* extract, *calendula officinalis* oil, candelilla (*euphorbia cerifera*) wax, canola oil, caprylic/capric triglyceride, cardamon (*elettaria cardamomum*) oil, carnauba (*copernicia cerifera*) wax, carrot (*daucus carota* sativa) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, eucalyptus globulus oil, evening primrose (*oenothera biennis*) oil, fatty acids, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica* limonum) oil, linoleic acid, linolenic acid, *macadamia ternifolia* nut oil, maltitol, matricaria (*chamomilla recutita*) oil, methyl glucose sesquistearate, methylsilanol PCA, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (citrus *aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinol palmitate, rice (*oryza sativa*) bran oil, RNA, rosemary (*rosmarinus officinalis*) oil, rose oil, safflower (*carthamus tinctorius*) oil, sage (*salvia officinalis*) oil, sandalwood (*santalum album*) oil, serine, serum protein, sesame (*sesamum indicum*) oil, shea butter (*butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus* dulcis) oil, synthetic beeswax, tocopherol, tocopheryl acetate, tocopheryl linoleate, tribehenin, tridecyl neopentanoate, tridecyl stearate, triethanolamine, tristearin, urea, vegetable oil (e.g., corn oil), water, waxes, wheat (*triticum vulgare*) germ oil and ylang ylang (*cananga odorata*) oil.

In some embodiments, a formulation comprises a moisturizing agent in an amount of about 0.05 to about 20 wt %, preferably about 1.0 to about 10 wt %, preferably about 0.1 to about 3.0 wt %, more preferably about 0.5, about 1.0, about 2.0 or about 2.5 wt %.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, butylated hydroxyanisole (BHA), butylated hydroxytoluene (BHT), t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite. In an exemplary embodiment, a formulation comprises BHT.

In some embodiments, a formulation comprises an antioxidant in amount of about 0.001 to about 1.0 wt %, preferably about 0.05 to about 0.75 wt % and more preferably about 0.1 wt % to about 0.5 wt %.

d. Structuring Agents

In some embodiments, a formulation comprises a structuring agent. In some embodiments, a structuring agent assists in providing rheological characteristics to the composition to contribute to the composition's stability. In other embodiments, a structuring agent can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

In some embodiments, a formulation comprises a structuring agent in amount of about 0.5 to about 15.0 wt %, preferably about 1.0 to about 10.0 wt %, more preferably about 2.0 to about 5.0 wt %.

e. Emulsifiers

In some embodiments, a formulation comprises an emulsifier. Emulsifiers can reduce the interfacial tension between phases and improve the formulation and stability of an emulsion. The emulsifiers can be nonionic, cationic, anionic, and zwitterionic emulsifiers. See, e.g., 2010 McCutcheon's Emulsifiers & Detergents North American edition (Mccutcheon's Emulsifiers and Detergents) (McCutcheon's Publications Apr. 1, 2010); and U.S. Pat. Nos. 5,011,681; 4,421,769 and 3,755,560. Topical formulations may include emulsifiers that act as stabilizers to enhance stability of the active agent or of the formulation itself. Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof. An exemplary emulsifier or surfactant is polyoxyl stearate (e.g., polyoxyl 40 stearate).

In some embodiments, a formulation comprises an emulsifying agent in amount from about 0.5 to about 2.5 wt %, preferably 0.5 to 2.0%, more preferably 1.0% or 1.8%.

f. Silicone Containing Compounds

In some embodiments, a formulation includes a silicone containing compound, i.e., any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

In some embodiments, a formulation comprises a silicone containing compound in an amount from about 0.1 to 15 wt %, preferably 0.1 to about 3.0 wt %, more preferably about 0.5, 1.0, or 2.5 wt %.

g. Essential Oils

In some embodiments, a formulation comprises an essential oil. Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° C. to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

In some embodiments, a formulation comprises an essential oil in amount of about 0.1 to about 15.0 wt %, preferably about 1.0 to about 10.0 wt % or preferably about 2.0 to about 5.0 wt %.

h. Thickening Agents

In some embodiments, a formulation comprises a thickening agent. Thickening agents, including thickener or gelling agents, include substances which that can increase the viscosity of a composition. Thickeners include those that can increase the viscosity of a composition without substantially modifying the efficacy of the active ingredient within the composition. Topical formulations may include thickening agents that act as stabilizers to enhance stability of the active agent or of the formulation itself. In certain aspects of the present invention, thickeners include hydrogenated polyisobutene or trihydroxystearin, or a mixture of both. One exemplary thickening agent is xanthan gum.

Non-limiting examples of additional thickening agents that can be used in the context of the present invention include carboxylic acid polymers, crosslinked polyacrylate polymers, polyacrylamide polymers, polysaccharides and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B.F. Goodrich).

In some embodiments, a formulation comprises a thickening agent in an amount of about 0.1 to about 20.0 wt %, preferably about 0.25 to about 10.0 wt %, more preferably from about 0.5 to about 5.0 wt %.

i. Hardeners and Plasticizers

In some embodiments, a formulation comprises a hardeners (also called a "stiffener") and/or a plasticizer or the like. Suitable hardeners include, for example, beeswax, an alcohol (e.g., cetyl alcohol, stearyl alcohol, myristyl alcohol), stearic acid, aluminium monostearate, bentonite or the like. Suitable plasticizers include, for example, glyceryl monostearate, polysorbate 80, propylene glycol or the like.

In some embodiments, a formulation comprises a hardener or a plasticizer in an amount of about 0.1 to about 15.0 wt %, preferably about 1.0 to about 10.0 wt %, more preferably about 2.0 to about 5.0 wt % j. Preservatives

In some embodiments, a formulation comprises a preservative. Useful preservatives known in the art include benzalkonium chloride, benzethonium, chlorohexidine, phenol, m-cresol, benzyl alcohol, methylparaben, propylparaben and other parabens, chlorobutanol, o-cresol, p-cresol, chlorocresol, phenylmercuric nitrate, thimerosal, benzoic acid, sorbic acid and various mixtures thereof. See, e.g., Wallhausser, K.-H., Develop. Biol. Standard, 24:9-28 (1974) (S. Krager, Basel). Preferably, the preservative is selected from methylparaben, propylparaben and mixtures thereof.

In some embodiments, a formulation comprises a preservative in an amount of about 0.01 to about 1.0 wt %, preferably from about 0.1 to 0.5 wt %, more preferably from about 0.03 to about 0.15 wt %. When alcohol is used as a preservative, the amount is usually about 15.0 to about 20.0%.

In some embodiments, a formulation comprises an active agent, a hardener, a structuring agent, a moisturizer, an emulsifier or surfactant, an antioxidant, a thickening agent, a preservative and a solvent. In some embodiments, a formulation comprises an active agent, a solvent and any combination of a hardener, a structuring agent, a moisturizer, an emulsifier, a surfactant, an antioxidant, a thickening agent and a preservative. In some embodiments, a formulation comprises an active agent, an emulsifier, a hardener, a thickening agent, an antioxidant, a thickening agent (or stabilizer), a preservative and a solvent, and in exemplary embodiments, the formulation further comprises more than one of any of these components. In exemplary embodiments, the solvent is water.

In some embodiments, a formulation comprises a RAR selective agonist, stearyl alcohol, stearic acid, isopropylmyristate, butylated hydroxytoluene, gum xanthan, polyoxyl stearate, sorbic acid, oil, and water. This formulation is particularly useful for making ointments.

Oral Administration

In one aspect, the invention provides an formulation comprising an active agent, such as a RAR selective agonist and a carrier medium, wherein the formulation is suitable for oral administration. Such oral formulations can be a solid, semisolid or liquid. Example dosage forms include tablets, lozenges, troches, pills, aqueous or oily suspensions, solid dispersions, granules, powders, emulsions, capsules, syrups, elixirs, gargle, sprays and gums. Pharmaceutically common capsules include gelatin hard capsules, soft gelatin capsules, starch capsules. The capsules may be filled with powders, granulates, pellets, tablets or a filling. The carrier medium in an oral formulation comprises one or more excipients, diluents, carriers, additives and combinations thereof known in the art that may be combined with an active agent (such as a RAR selective agonist disclosed herein) to enhance, facilitate or enable the production, storage, administration, delivery or effectiveness of the active compound.

An oral formulation typically comprises a carrier medium in the range of from about 70% to about 99.9% (w/w), preferably from about 80% to about 95% (w/w) of the formulation. In some embodiments, a RAR selective agonist is present in a range selected from about 1 mg/mL to about 200 mg/mL, about 10 mg/mL to about 175 mg/mL, about 20 mg/mL to about 150 mg/mL, about 30 mg/mL to about 125 mg/mL, about 40 mg/mL to about 100 mg/mL and about 50 mg/mL to about 75 mg/mL. In one embodiment, a formulation comprises a RAR selective agonist at a concentration selected from about 1 mg/mL, about 2 mg/mL, about 2.5 mg/mL, about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 75 mg/mL, about 80 mg/mL, about 90 mg/mL, about 100 mg/mL, about 120 mg/mL, about 125 mg/mL, about 150 mg/mL, about 175 mg/mL and about 200 mg/mL.

In some embodiments, a RAR selective agonist is present in a range selected from about 1 mg/g to about 250 mg/g, or optionally about 20 mg/g to about 200 mg/g, or about 40 mg/g to about 180 mg/g, or about 60 mg/g to about 160 mg/g, or about 80 mg/g to about 130 mg/g, or about 50 mg/g to about 100 mg/g. In one embodiment, a formulation comprises a RAR selective agonist at a concentration of about 133 mg/g, about 185 mg/g, about 200 mg/g, and about 250 mg/g. Exemplary amounts of RAR selective agonist include, without limitation, about 20 mg/g, about 50 mg/g, about 75 mg/g, about 100 mg/g, about 120 mg/g, about 130 mg/g, about 140 mg/g, about 150 mg/g, about 175 mg/g and about 200 mg/g.

In some embodiments, the formulation comprises an excipient. Excipients commonly used to formulate such dosage forms include encapsulating materials or formulation additives such as absorption accelerators, antioxidants, binders, buffers, coating agents, coloring agents, diluents, disintegrating agents, emulsifiers, extenders, fillers, flavoring agents, humectants, lubricants, preservatives, propellants, releasing agents, sterilizing agents, sweeteners, solubilizers and mixtures thereof. Examples of specific excipients include agar, alginic acid, aluminum hydroxide, benzyl benzoate, 1,3-butylene glycol, castor oil, cellulose, cellulose acetate, cocoa butter, corn starch, corn oil, cottonseed oil, ethanol, ethyl acetate, ethyl carbonate, ethyl cellulose, ethyl laureate, ethyl oleate, gelatin, germ oil, glucose, glycerol, groundnut oil, isopropanol, isotonic saline, lactose, magnesium hydroxide, magnesium stearate, malt, olive oil, peanut oil, potassium phosphate salts, potato starch, propylene glycol, talc, tragacanth, water, safflower oil, sesame oil, sodium carboxymethyl cellulose, sodium lauryl sulfate, sodium phosphate salts, soybean oil, sucrose, tetrahydrofurfuryl alcohol, and mixtures thereof.

In some embodiments, the formulation comprises a diluent. Suitable diluents illustratively include, either individually or in combination, lactose, including anhydrous lactose and lactose monohydrate; lactitol; maltitol; mannitol; sorbitol; xylitol; dextrose and dextrose monohydrate; fructose; sucrose and sucrose-based diluents such as compressible sugar, confectioner's sugar and sugar spheres; maltose; inositol; hydrolyzed cereal solids; starches (e.g., corn starch, wheat starch, rice starch, potato starch, tapioca starch, etc.), starch components such as amylose and dextrates, and modified or processed starches such as pregelatinized starch; dextrins; celluloses including powdered cellulose, microcrystalline cellulose, silicified microcrystalline cellulose, food grade sources of α- and amorphous cellulose and powdered cellulose, and cellulose acetate; calcium salts including calcium carbonate, tribasic calcium phosphate, dibasic calcium phosphate dihydrate, monobasic calcium sulfate monohydrate, calcium sulfate and granular calcium lactate trihydrate; magnesium carbonate; magnesium oxide; bentonite; kaolin; sodium chloride; and the like. Such diluents, if present, typically constitute in total about 5% to about 95%, for example about 20% to about 90%, or about 50% to about 85%, by weight of the composition. The diluent or diluents selected preferably exhibit suitable flow properties and, where tablets are desired, compressibility.

In some embodiments, the formulation comprises disintegrant. Suitable disintegrants include, either individually or in combination, starches including pregelatinized starch and sodium starch glycolate; clays; magnesium aluminum silicate; cellulose-based disintegrants such as powdered cellulose, microcrystalline cellulose, methylcellulose, low-substituted hydroxypropylcellulose, carmellose, carmellose calcium, carmellose sodium and croscarmellose sodium; alginates; povidone; crospovidone; polacrilin potassium; gums such as agar, guar, locust bean, karaya, pectin and tragacanth gums; colloidal silicon dioxide; and the like. One or more disintegrants, if present, typically constitute in total about 0.2% to about 30%, for example about 0.5% to about 20%, or about 1% to about 10%, by weight of the composition.

In some embodiments, the formulation comprises a binding agent or adhesive. Binding agents or adhesives are useful excipients, particularly where the composition is in the form of a tablet. Such binding agents and adhesives should impart sufficient cohesion to the blend being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; glucose; polydextrose; starch including pregelatinized starch; gelatin; modified celluloses including methylcellulose, carmellose sodium, hydroxypropylmethylcellulose (HPMC), hydroxypropylcellulose, hydroxyethylcellulose and ethylcellulose; dextrins including maltodextrin; zein; alginic acid and salts of alginic acid, for example sodium alginate; magnesium aluminum silicate; bentonite; polyethylene glycol (PEG); polyethylene oxide; guar gum; polysaccharide acids; polyvinylpyrrolidone (povidone or PVP), for example povidone K-15, K-30 and K-29/32; polyacrylic acids (carbomers); polymethacrylates; and the like. One or more binding agents and/or adhesives, if present, typically constitute in total about 0.5% to about 25%, for example about 1% to about 15%, or about 1.5% to about 10%, by weight of the composition.

In some embodiments, the formulation comprises a wetting agent. Wetting agents are normally selected to maintain the drug in close association with water, a condition that can improve bioavailability of the composition. Non-limiting examples of surfactants that can be used as wetting agents include, either individually or in combination, quaternary ammonium compounds, for example benzalkonium chloride, benzethonium chloride and cetylpyridinium chloride; dioctyl sodium sulfosuccinate; polyoxyethylene alkylphenyl ethers, for example nonoxynol 9, nonoxynol 10 and octoxynol 9; poloxamers (polyoxyethylene and polyoxypropylene block copolymers); polyoxyethylene fatty acid glycerides and oils, for example polyoxyethylene (8) caprylic/capric mono- and diglycerides, polyoxyethylene (35) castor oil and polyoxyethylene (40) hydrogenated castor oil; polyoxyethylene alkyl ethers, for example ceteth-10, laureth-4, laureth-23, oleth-2, oleth-10, oleth-20, steareth-2, steareth-10, steareth-20, steareth-100 and polyoxyethylene (20) cetostearyl ether; polyoxyethylene fatty acid esters, for example polyoxyethylene (20) stearate, polyoxyethylene (40) stearate and polyoxyethylene (100) stearate; sorbitan esters, for example sorbitan monolaurate, sorbitan monooleate, sorbitan monopalmitate and sorbitan monostearate; polyoxyethylene sorbitan esters, for example polysorbate 20 and polysorbate 80; propylene glycol fatty acid esters, for example propylene glycol laurate; sodium lauryl sulfate; fatty acids and salts thereof, for example oleic acid, sodium oleate and triethanolamine oleate; glyceryl fatty acid esters, for example glyceryl monooleate, glyceryl monostearate and glyceryl palmitostearate; α-tocopherol polyethylene glycol (1000) succinate (TPGS); tyloxapol; and the like. One or more wetting agents, if present, typically constitute in total about 0.1% to about 15%, for example about 0.2% to about 10%, or about 0.5% to about 7%, by weight of the composition.

Nonionic surfactants, more particularly poloxamers, are examples of wetting agents that can be useful herein. Illustratively, a poloxamer such as Pluronic™ F127, if present, can constitute about 0.1% to about 10%, for example about 0.2% to about 7%, or about 0.5% to about 5%, by weight of the composition.

In some embodiments, the formulation comprises a lubricant. Lubricants reduce friction between a tableting mixture and tableting equipment during compression of tablet formulations. Suitable lubricants include, either individually or in combination, glyceryl behenate; stearic acid and salts thereof, including magnesium, calcium and sodium stearates; hydrogenated vegetable oils; glyceryl palmitostearate; talc; waxes; sodium benzoate; sodium acetate; sodium fumarate; sodium stearyl fumarate; PEGs (e.g., PEG 4000 and PEG 6000); poloxamers; polyvinyl alcohol; sodium oleate; sodium lauryl sulfate; magnesium lauryl sulfate; and the like. One or more lubricants, if present, typically constitute in total about 0.05% to about 10%, for example about 0.1% to about 5%, or about 0.2% to about 2%, by weight of the composition. Sodium stearyl fumarate is a particularly useful lubricant.

In some embodiments, the formulation comprises an anti-adherent. Anti-adherents reduce sticking of a tablet formulation to equipment surfaces. Suitable anti-adherents include, either individually or in combination, talc, colloidal silicon dioxide, starch, DL-leucine, sodium lauryl sulfate and metallic stearates. One or more anti-adherents, if present, typically constitute in total about 0.05% to about 10%, for example about 0.1% to about 7%, or about 0.2% to about 5%, by weight of the composition. Colloidal silicon dioxide is a particularly useful anti-adherent.

In some embodiments, the formulation comprises a glidant. Glidants improve flow properties and reduce static in a tableting mixture. Suitable glidants include, either individually or in combination, colloidal silicon dioxide, starch, powdered cellulose, sodium lauryl sulfate, magnesium trisilicate and metallic stearates. One or more glidants, if present, typically constitute in total about 0.05% to about 10%, for example about 0.1% to about 7%, or about 0.2% to about 5%, by weight of the composition. Colloidal silicon dioxide is a particularly useful glidant.

Other excipients such as buffering agents, stabilizers, antioxidants, antimicrobials, colorants, flavors and sweeteners are known in the pharmaceutical art and can be used in the present embodiments. Tablets can be uncoated or can comprise a core that is coated, for example with a nonfunctional film or a release-modifying or enteric coating. Capsules can have hard or soft shells comprising, for example, gelatin (in the form of hard gelatin capsules or soft elastic gelatin capsules), starch, carrageenan and/or HPMC, optionally together with one or more plasticizers.

In some embodiments, the formulation comprises an agent for enhancing palatability, such as masking agents. A masking agent may include one or more organic acids, including amino acids. Organic acids of interest include, but are not limited to: glycolic acid, lactic acid, methyl lactic acid, palycarboxlyic acids, e.g., malic acid, citric acid, tartronic acid, tartaric acid, succinic acidetc. Amino acids of interest include, but are not limited to: glycine, alanine, valine, leucine, isoleucine, serine, threonine, cysteine, cystine, methionine, aspartic acid, asparagine, glutamic acid, glutamine, arginine, lysine, 5-hydroxylysine, histidine, phenylalanine, tyrosine, tryptophan, 3-hydroxyproline, 4-hydroxyproline, proline, homocysteine, homocystine, homoserine, ornithine, citrulline, creatine, asparaginic acid, 3-aminopropanoic acid, theanine, 2-aminobutanoic acid, 4-aminobutanoic acid, 2-amino-2-methylpropanoic acid, 2-methyl-3-aminopropanoic acid, 2,6-diaminopimelic acid, 2-amino-3-phenylbutanoic acid, phenylglycine, canavanine, canaline, 4-hydroxyarginine, 4-hydroxyornithine, homoarginine, 4-hydroxyhomoarginine, β-lysine, 2,4-diaminobutanoic acid, 2,3-diaminopropanoic acid, 2-methylserine, 3-phenylserine betaine, sulfur-containing amino acids, such as taurine, cysteinesulfinic acid, methionine sulfoxide and methionine sulfone. A masking agent can also be a saccharide or polysaccharide, such as cyclodextrin. A formulation may also comprise a sweetening agent such as fructose, aspartame or saccharin; flavoring agents such as peppermint, oil of wintergreen, or cherry coloring agents and preserving agents, to provide a pharmaceutically palatable preparation.

In some embodiments, a formulation is a capsule comprising a capsule shell and a filling. In exemplary embodiments, the filling comprises, in any combination, a dispersing agent (e.g., cellulose and its derivatives, such as carboxymethylcellulose and natural gums); a solubilizing/oral absorption promoter agent (e.g., cyclodextrins, ethanol, triacetin, propylen glycol, glycerides, medium and long chain fatty acid, polyoxyethylene hydrogenated or non-hydrogenated vegetable oils derivatives); a surfactant (e.g., poloxamers, medium chain triglycerides, ethoxylated esters, polyglycerol esters, polyoxyethylene alkyl ethers, sorbitan esters, polyoxyethylene sorbitan fatty acid esters); and a viscosity modifier (hydrogenated or non-hydrogenated vegetable oils, glycerol esters, polyglycerol esters and propylene glycol esters). The filling may also optionally contain chemical stabilizing-promoting agents such as antioxidants and chelating agents.

In various embodiments, a formulation (especially a tablet, pill or capsule) comprises a coating. The coating can be formulated in order to control delivery of the active, whether rapid or slow, sustained release is desired. In some embodiments, the oral formulation is a tablet, pill or capsule coated to delay disintegration and absorption in the gastrointestinal tract, thereby providing a sustained action over an extended period of time. Selectively permeable membranes surrounding an osmotically active driving compound are also suitable for orally administered compounds. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Polymeric materials that can be used for sustained release include but are not limited to, sodium carboxymethylcellulose, hydroxypropylcellulose, hydroxypropylmethylcellulose and hydroxyethylcellulose (preferably, hydroxypropyl methylcellulose). Coating materials for sustained release include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In some embodiments, a formulation is a rapid release oral formulation. In these embodiments, the formulation comprises a coating that either dissolves independently of the pH value or is removed from the solid oral formulation upon contact with digestive juice. In this way, relatively rapid disintegration of the drug form and release of the active substance within a short period of time are ensured, whereby high local concentrations of the active substance are achieved. The coating may be applied using methods such as film coating, press coating, tablet coating, encapsulating or micro-encapsulating. The release of active substance from the appropriately coated solid administration forms for oral application, such as film tablets, coated tablets, laminated tablets, capsules, or microcapsules, takes place more rapidly as compared to the gastric juice-resistant administration forms. Film-forming agents (i.e., coatings) for coating tablets include those derived from, e.g., the groups of cellulose derivatives, dextrins, starches and starch derivatives, polymers based on other carbohydrates and derivatives thereof, natural gums such as gum arabic, xanthans, alginates; polyacrylic acid, polyvinyl alcohol, polyvinyl acetate, polyvinylpyrrolidone, polymethacrylates and derivatives thereof (Eudragit®), chitosan and derivatives thereof, shellac and derivatives thereof. In addition to these film-forming agents, substances from the class of wax and fat substances may be used to produce the coatings according to the invention. In some embodiments, the cellulose derivative is selected from soluble alkyl- or hydroxyalkylcellulose derivatives such as methylcellulose, hydroxymethylcellulose, hydroxyethylcellulose, hydroxypropylcellulose, methylhydroxyethylcellulose, methylhydroxypropylcellulose, or sodium carboxymethylcellulose. In exemplary embodiments, methylhydroxypropylcellulose is employed. The usual cellulose derivatives suitable for pharmaceutical purposes, with varying degrees of substitution and/or varying molecular weights corresponding to varying viscosity levels of the aqueous solutions, may be used as suitable film-forming agents on the basis of cellulose. Likewise, insoluble cellulose derivatives such as ethylcellulose may be employed.

If required, the films may contain additional adjuvants such as plasticizers, pore-forming agents, filling agents, colorants, pigments, antifoam agents, antistick agents, and the like. The various polymers, adjuvants, excipients and additives described through the present disclosure may be used in this respect. In addition, all the pharmaceutically common or physiologically tolerable adjuvants which are suited to form a closed coat by press coating on the drug forms to be covered may be used. In particular, these include adjuvants as are common in conventional tabletting, specifically filling agents from the group of carbohydrates such as lactose, saccharose, glucose and other sugars, microcrystalline cellulose, starches and starch derivatives, sugar alcohols such as mannitol, sorbitol, xylitol, inorganic filling agents such as phosphates and carbonates. Other adjuvants as required in the production of conventional tablets, such as binding agents, disintegrants, flow agents, release agents, taste improvers, pigments, and coloring agents may be contained in addition to the filling agents.

In some embodiments, the formulation comprises a stabilizer. Examples include those selected from lecithins; phospholipids; pharmaceutical acceptable oils, e.g. soybean oils and the like, polyethylenglycols and saturated or insaturated mono-, di- or triglicerides. Other stabilizers disclosed herein may also be used.

In some embodiments, the formulation comprises a RAR selective agonist and a carrier, wherein the drug is in solution in the carrier. This will be understood to mean that substantially all of the drug is in solution, i.e., no substantial portion, for example no more than about 2%, or no more than about 1%, of the drug is in solid (e.g., crystalline) form, whether dispersed, for example in the form of a suspension, or not. In practical terms, this means that the drug must normally be formulated at a concentration below its limit of solubility in the carrier. It will be understood that the limit of solubility can be temperature-dependent, thus selection of a suitable concentration should take into account the range of temperatures to which the composition is likely to be exposed in normal storage, transport and use.

In some embodiments, the formulation comprises water.

In some embodiments, the formulation comprises an organic solvent. Among preferred water-soluble organic solvents are ethanol, benzyl alcohol, dimethylacetamide, PVP, PG and PEG compounds such as: PEG 300, PEG 400, or PEG 400 monolaurate. The PEG compound in the present compositions is provided in an amount of about 5% to about 100%, or about 5% to about 60%, or about 10% to about 90%, or about 20% to about 80%, or 30% to about 70%, or about 40% to about 60%, all concentrations being a percentage of volume/volume (v/v). PG may be present at a concentration of about 2.5% to about 100% (v/v).

The concentration of the PEG compounds in the present compositions can vary depending on what other solubilizers or diluents or excipients are also present. For example, the PEG 300, PEG 400 or PEG 400 monolaurate of the present invention can be at a concentration of about 5%, about 10%, about 12.5%, about 15%, about 20%, about 25%, about 30%, about 35%, about 40%, about 45%, about 50%, about 55%, about 60%, about 65%, about 70%, about 75%, about 80%, about 85%, about 90%, or about 95%, all such concentrations being given as a percentage of volume/volume (v/v).

In some embodiments, the formulation is substantially non-aqueous, i.e., having no water, or having an amount of water that is small enough to be, in practical terms, essentially non-deleterious to performance or properties of the composition. Typically, the carrier comprises zero to less than about 5% by weight water. It will be understood that certain ingredients useful herein can bind small amounts of water on or within their molecules or supramolecular structures; such bound water if present does not affect the "substantially non-aqueous" character of the carrier as defined herein. Suitable examples of long chain triglycerides include any pharmaceutically acceptable vegetable oil, for example canola, coconut, corn, cottonseed, flaxseed, olive, palm, peanut, safflower, sesame, soy and sunflower oils, and mixtures of such oils. Oils of animal, particularly marine animal, origin can also be used, including for example fish oil.

In some embodiments, the formulation comprises one or more glyceride materials. Suitable glyceride materials include, without limitation, medium to long chain mono-, di- and triglycerides. The term "medium chain" herein refers to hydrocarbyl chains individually having no less than about 6 and less than about 12 carbon atoms, including for example $C_8$ to $C_{10}$ chains. Thus glyceride materials comprising caprylyl and capryl chains, e.g., caprylic/capric mono-, di- and/or triglycerides, are examples of "medium chain" glyceride materials herein. The term "long chain" herein refers to hydrocarbyl chains individually having at least about 12, for example about 12 to about 18, carbon atoms, including for example lauryl, myristyl, cetyl, stearyl, oleyl, linoleyl and linolenyl chains. Medium to long chain hydrocarbyl groups in the glyceride materials can be saturated, mono- or polyunsaturated.

In some embodiments, a formulation comprises a phospholipid or mixture of phospholipids. In general such phospholipids are phosphoric acid esters that yield on hydrolysis phosphoric acid, fatty acid(s), an alcohol and a nitrogenous base. Pharmaceutically acceptable phospholipids can include without limitation phosphatidylcholines, phosphatidylserines and phosphatidylethanolamines. In one embodiment the composition comprises phosphatidylcholine, derived for example from natural lecithin. Any source of lecithin can be used, including animal sources such as egg yolk, but plant sources are generally preferred. Soy is a particularly rich source of lecithin that can provide phosphatidylcholine for use in the present invention.

Illustratively, a suitable amount of phospholipid is about 15% to about 75%, for example about 30% to about 60%, by weight of the carrier, although greater and lesser amounts can be useful in particular situations.

In some embodiments, a formulation comprises a glycol. Generally, glycols tend to be suitable only for non-encapsulated formulations or where a soft capsule shell is to be used, and tend to be incompatible with hard shells such as hard gelatin shells. Suitable glycols include propylene glycol and polyethylene glycols (PEGs) having molecular weight of about 200 to about 1,000 g/mol, e.g., PEG-400, which has an average molecular weight of about 400 g/mol. Such glycols can provide relatively high solubility of the drug; however the potential for oxidative degradation of the drug can be increased when in solution in a carrier comprising such glycols, for example because of the tendency of glycols to produce superoxides, peroxides and/or free hydroxyl radicals. The higher the glycol content of the carrier, the greater may be the tendency for degradation of a chemically unstable drug. In one embodiment, therefore, one or more glycols are present in a total glycol amount of at least about 1% but less than about 50%, for example less than about 30%, less than about 20%, less than about 15% or less than about 10% by weight of the carrier. In another embodiment, the carrier comprises substantially no glycol.

Glycolides are glycols such as propylene glycol or PEG esterified with one or more organic acids, for example medium- to long-chain fatty acids. Suitable examples include propylene glycol monocaprylate, propylene glycol monolaurate and propylene glycol dilaurate products such as, for example. Capmul PG8™, Capmul PG12™ and Capmul PG-2L™ respectively of Abitec Corp. and products substantially equivalent thereto.

Suitable glyceride materials for use together with a phospholipid include, without limitation, those mentioned above. Glyceride materials such as medium chain and/or long chain mono-, di- and triglycerides, more typically medium-chain mono-, di- and triglycerides, can be present in a total glyceride amount of about 5% to about 70%, for example about 15% to about 60% or about 25% to about 50%, by weight of the carrier, although greater and lesser amounts can be useful in particular situations. In one embodiment, the encapsulated liquid comprises about 7% to about 30%, for example about 10% to about 25%, by weight medium-chain triglycerides and about 7% to about 30%, for example about 10% to about 25%, by weight medium-chain mono- and diglycerides.

Additional solubilizing agents that are other than glycols, glycolides or glyceride materials can be included if desired. Such agents, for example N-substituted amide solvents such as dimethylformamide (DMF) and N,N-dimethylacetamide (DMA), can, in specific cases, assist in raising the limit of solubility of the drug in the carrier, thereby permitting increased drug loading. However, the carriers useful herein generally provide adequate solubility of small-molecule drugs of interest herein without such additional agents.

In some embodiments, the formulation comprises a viscosity reducing agent. An example of such an agent is an alcohol, more particularly ethanol, which is preferably introduced in a form that is substantially free of water, for example 99% ethanol, dehydrated alcohol USP or absolute ethanol. Excessively high concentrations of ethanol should, however, generally be avoided. This is particularly true where, for example, the drug-carrier system is to be administered in a gelatin capsule, because of the tendency of high ethanol concentrations to result in mechanical failure of the capsule. In general, suitable amounts of ethanol are 0% to about 25%, for example about 1% to about 20% or about 3% to about 15%, by weight of the carrier. Glycols such as propylene glycol or PEG and medium-chain mono- and diglycerides (for example caprylic/capric mono- and diglycerides) can also be helpful to lower viscosity; where the drug-carrier system is to be encapsulated in a hard capsule such as a hard gelatin capsule, medium-chain mono- and diglycerides are particularly useful in this regard.

In some embodiments, the formulation comprises a non-phospholipid surfactant. Such a surfactant can serve various functions, including for example enhancing dispersion of the encapsulated liquid upon release from the capsule in the aqueous environment of the gastrointestinal tract. Thus in one embodiment the non-phospholipid surfactant is a dispersing and/or emulsifying agent that enhances dispersion and/or emulsification of the capsule contents in real or simulated gastrointestinal fluid. Illustratively, a surfactant such as a polysorbate (polyoxyethylene sorbitan ester), e.g., polysorbate 80 (available for example as Tween 80™ from Uniqema), can be included in an amount of 0% to about 30%, for example about 7% to about 30% or about 10% to about 25%, by weight of the carrier. In some embodiments such a surfactant is included in an amount of 0% to about 5%, for example 0% to about 2% or 0% to about 1%, by weight of the carrier.

Other surfactants may be suitable and include, either individually or in combination, quaternary ammonium compounds, for example benzalkonium chloride, benzethonium chloride and cetylpyridinium chloride; dioctyl sodium sulfosuccinate; polyoxyethylene alkylphenyl ethers, for example nonoxynol 9, nonoxynol 10 and octoxynol 9; poloxamers (polyoxyethylene and polyoxypropylene block copolymers), for example poloxamer 188 and poloxamer 237; polyoxyethylene fatty acid glycerides and oils, for example polyoxyethylene (8) caprylic/capric mono- and diglycerides, polyoxyethylene (35) castor oil and polyoxyethylene (40) hydrogenated castor oil; polyoxyethylene alkyl ethers, for example ceteth-10, laureth-4, laureth-23, oleth-2, oleth-10, oleth-20, steareth-2, steareth-10, steareth-20, steareth-100 and polyoxyethylene (20) cetostearyl ether; polyoxyethylene fatty acid esters, for example polyoxyethylene (20) stearate, polyoxyethylene (40) stearate and polyoxyethylene (100) stearate; sorbitan esters, for example sorbitan monolaurate, sorbitan monooleate, sorbitan monopalmitate and sorbitan monostearate; polyoxyethylene sorbitan esters, for example polysorbate 20 and polysorbate 80; propylene glycol fatty acid esters, for example propylene glycol laurate; sodium lauryl sulfate; fatty acids and salts thereof, for example oleic acid, sodium oleate and triethanolamine oleate; glyceryl fatty acid esters, for example glyceryl monooleate, glyceryl monostearate and glyceryl palmitostearate; α-tocopheryl polyethylene glycol succinate (TPGS); tyloxapol; and the like. In one embodiment, the at least one surfactant is a poloxamer or mixture of poloxamers. Poloxamer 188 is a specific example. One or more surfactants typically constitute in total about 10 to about 100 mg/ml of the suspension. In the case of poloxamer 188, an illustratively suitable amount is about 10 to about 100 mg/ml, for example about 15 to about 60 mg/ml, of the suspension. The surfactant can be present in any desired effective amount, such as at a concentration of about 1% (v/v) to about 100% (v/v), preferably about 9% (v/v) to about 80% (v/v), and more preferably, about 10% (v/v) to about 50% (v/v). As specific examples, preferred concentrations of a non-ionic surfactant are Tween® 20 at a concentration of about 9% (v/v) to about 100% (v/v) and Tween® 80 of about 33% (v/v) to about 100% (v/v). All percentages of the surfactant are volume percentages (v/v).

In some embodiments, the formulation comprises a cyclodextrin. The cyclodextrins herein may be α-cyclodextrin, β-cyclodextrin, γ-cyclodextrin, and the modified cyclodextrins may include HP-β-CD and SBE-β-CD, for example. In one embodiment, the present composition contains a modified cyclodextrin in a concentration of about 5% to about 80%, or about 10% to about 70%, or about 20% to about 60%, or about 30% to about 50%, all such concentrations being given as a percentage of weight/volume (w/v).

In some embodiments, the formulation comprises a modified cellulose, such as EC, HPMC, MC and CMC. The modified cellulose can be present in any desired effective amount, such as a concentration of about 0.1% to about 25%, or about 0.5% to about 7.5%, or about 1.0% to about 5%. As specific examples, EC may be present at a concentration of about 5% to about 20%; HPMC may be present at a concentration of about 0.5% to about 1%; MC may be present at a concentration of about 1% to about 3%; and CMC may be present at a concentration of about 1% to about 4%. The percentages of modified cellulose are in weight per volume (w/v).

In another embodiment, the formulation comprise a water-insoluble lipid, such as an oil, fat emulsion or wax. The water-insoluble lipid carriers can be present in any desired effective amount, such as a concentration of about 10% to about 100%, or about 15% to about 85%, or about 25% to about 75%. Non-limiting examples of oils include corn oil, olive oil, peppermint oil, soy bean oil, sesame seed oil, mineral oil and glycerol. In one embodiment, the oil is present at a concentration of about 10% (v/v) to about 100% (v/v). Mixed fat emulsion compositions are available, such as Intralipid® emulsion, as described above. In various embodiments, mixed fat emulsions may be present at a concentration of about 10% (w/v) to about 30% (w/v); and preferably about 20% (w/v). Non-limiting examples of suitable waxes are beeswax and carnuba wax. In one embodiment, the wax is present at a concentration of about 5% (w/w) to about 50% (w/w).

In some embodiments, the formulation is a solid dispersion. Solid dispersions comprise a RAR selective agonist in an essentially non-crystalline or amorphous form, which is usually more soluble than the crystalline form. The term "solid dispersion" herein encompasses systems having small solid-state particles of one phase dispersed in another solid-state phase. More particularly, the present solid dispersions comprise one or more active ingredients dispersed in an inert carrier or matrix in solid state, and can be prepared by melting or solvent methods or by a combination of melting and solvent methods.

The major component of the matrix of a solid dispersion product is a polymer that is hydrophilic or water-soluble at least in a part of the pH scale, more particularly at a pH occurring in the gastrointestinal (GI) tract, or a combination of such polymers. A polymer or polymer mixture useful herein is solid at ambient temperature and, in the interests of good storage stability at a range of temperatures, should remain solid even at the highest temperatures typically experienced during storage, transport and handling of the product. A useful property of a polymer determining its usefulness herein is therefore its glass transition temperature ($T_g$). Suitable water-soluble polymers include, but are not limited to, those having a $T_g$ of at least about 50° C., more particularly about 80° C. to about 180° C. Methods for determining $T_g$ values of organic polymers are described for example in Sperling, ed. (1992) *Introduction To Physical Polymer Science*, 2nd edition, John Wiley & Sons, Inc. Exemplary polymers include homopolymers and copolymers of N-vinyl lactams, especially homopolymers and copolymers of N-vinyl pyrrolidone, e.g., the homopolymer polyvinylpyrrolidone (PVP or povidone) and copolymers such as those comprising monomers of N-vinyl pyrrolidone and vinyl acetate (copovidone) or N-vinyl pyrrolidone and vinyl propionate; cellulose esters and cellulose ethers, in particular methylcellulose, ethylcellulose, (hydroxyalkyl)celluloses such as hydroxypropylcellulose, (hydroxyalkyl)alkyl-celluloses such as hydroxypropylmethylcellulose (HPMC or hypromellose), cellulose phthalates and succinates such as cellulose acetate phthalate, hydroxypropylmethylcellulose phthalate, hydroxypropylmethylcellulose succinate and hydroxypropylmethylcellulose acetate succinate (HPMC-AS); high molecular weight polyalkylene oxides such as polyethylene oxide, polypropylene oxide and copolymers of ethylene oxide and propylene oxide (poloxamers); polyacrylates and polymethacrylates such as methacrylic acid/ethyl acrylate copolymers, methacrylic acid/methyl methacrylate copolymers, butyl methacrylate/2-dimethylaminoethyl methacrylate copolymers, poly(hydroxyalkyl acrylates) and poly(hydroxyalkyl methacrylates); polyacrylamides; vinyl acetate polymers such as copolymers of vinyl acetate and crotonic acid, partially hydrolyzed polyvinyl acetate (also referred to as partially saponified "polyvinyl alcohol") and polyvinyl alcohol; oligo- and polysaccharides such as carrageenans, galactomannans and xanthan gum; and mixtures of two or more thereof.

The dispersion, and other formulations, may further comprise a non-ionic surfactant as disclosed herein.

As can be appreciated by one of skill in the art, an excipient, carrier, diluent or additive that is suitable for topical formulations may also in some instances be suitable for oral formulations, and an excipient, carrier, diluent or additive that is suitable for oral formulations may also in some instances be suitable for topical formulations.

In one aspect, the invention provides a RAR selective agonist as disclosed herein for treating a disease in a subject. In one aspect, the invention provides a formulation of a RAR selective agonist as disclosed herein for treating a disease in a subject. In one aspect, the invention provides a RAR selective agonist as disclosed herein for use in manufacturing a medicament for treating a disease in a subject. In one aspect, the invention provides a formulation of a RAR selective agonist as disclosed herein for use in manufacturing a medicament for treating a disease in a subject.

In one aspect, the invention provides a RAR selective agonist as disclosed herein for preventing a disease in a subject. In one aspect, the invention provides a formulation of a RAR selective agonist as disclosed herein for preventing a disease in a subject. In one aspect, the invention provides a RAR selective agonist as disclosed herein for use in manufacturing a medicament for preventing a disease in a subject. In one aspect, the invention provides a formulation of a RAR selective agonist as disclosed herein for use in manufacturing a medicament for preventing a disease in a subject.

In one aspect, the invention provides a RAR selective agonist as disclosed herein for inducing a medically beneficial effect in a subject. In one aspect, the invention provides a formulation of a RAR selective agonist as disclosed herein for inducing a medically beneficial effect in a subject. In one aspect, the invention provides a RAR selective agonist as disclosed herein for use in manufacturing a medicament for inducing a medically beneficial effect in a subject. In one aspect, the invention provides a formulation of a RAR selective agonist as disclosed herein for use in manufacturing a medicament for inducing a medically beneficial effect in a subject.

Devices

In one aspect, the invention provides a medical device comprising a RAR selective agonist or a formulation thereof. In exemplary embodiments, the medical device is a stent. A variety of stents known in the art can be used in the present invention, and the underlying structure of the stent can be virtually any stent design, whether of the self-expanding type or of the balloon-expandable type and whether metal or polymeric. The stent could be made of virtually any bio-compatible material having physical properties suitable for the design. For example, tantalum and stainless steel have been proven suitable for many such designs and could be used in the present invention. Also, stents made with biostable or bioabsorbable polymers such as poly(ethylene terephthalate), polyacetal, poly(lactic acid), poly(ethylene oxide)/poly(butylene terephthalate) copolymer could be used in the present invention. Although the stent surface should be clean and free from contaminants that may be introduced during manufacturing, the stent surface requires no particular surface treatment in order to retain the coating applied in the present invention. Both the inner and outer surfaces of the stent may be provided with the coating according to the present invention.

Particularly useful stents include those that are suitable for controlled-release of a drug, such as a RAR selective agonist. In exemplary embodiments, a stent comprises, in addition to the drug, a carrier, such as a coating carrier, or a matrix. Some materials suitable for the coating carrier are presently in clinical use for the slow release of drugs, for example, from capsules, tablets, powders, or other galenic preparations after internal application into the gastrointestinal tract, such as gelatin, cellulose and methacrylic acid. Synthetic polymers have been developed which are degradable within the body, for use as drug carriers. Incorporating drugs into carrier substances, and using powders and micro-beads for timed, continuous release, have been described.

The coating carrier can include a solvent and a synthetic or naturally occurring polymer. The polymer chosen must be a polymer that is biocompatible and minimizes irritation to the vessel wall when the stent is implanted. The polymer may be either a biostable or a bioabsorbable polymer depending on the desired rate of release or the desired degree of polymer stability. Bioabsorbable polymers that could be used include poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g. PEO/PLA), polyalkylene oxalates, polyphosphazenes and biomolecules such as fibrin, fibrinogen, cellulose, starch, collagen and hyaluronic acid. Also, biostable polymers with a relatively low chronic tissue response such as polyurethanes, silicones, and polyesters could be used and other polymers could also be used if they can be dissolved and cured or polymerized on the stent such as polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon, rayon-triacetate; cellulose, cellulose acetate, cellulose butyrate; cellulose acetate butyrate; cellophane; cellulose nitrate; cellulose propionate; cellulose ethers; and carboxymethyl cellulose. In some embodiments, the polymer is biodegradeable and will disintegrate, with consequent slow release of drugs incorporated therein, while in contact with blood or other body fluids. The active period of the coated stent may be adjusted by varying the thickness of the coating, the specific type of material selected for the carrier, and the time release characteristics of specific substances incorporated into the carrier.

The ratio of therapeutic substance to polymer in the solution will depend on the efficacy of the polymer in securing the therapeutic substance onto the stent and the rate at which the coating is to release the therapeutic substance to the tissue of the blood vessel. More polymer may be needed if it has relatively poor efficacy in retaining the therapeutic substance on the stent and more polymer may be needed in order to provide an elution matrix that limits the elution of a very soluble therapeutic substance. The weight proportion of drug relative to the combination of drug and carrier can range from about 90% to about 1%. Other useful proportions include about 5%, about 10%, about 20%, about 30%, about 40%, about 50%, about 60%, about 70% and about 80%.

Olejnik, US 20080213338 A1, describes an implant stent with a retinoid for improved biocompatibility, and similar structures may be useful for constructing stents comprising a RAR selective agonist or a formulation thereof as disclosed herein.

Uses

The retinoids according to the invention possess RAR agonist activity. RARγ receptor is expressed in highest level in skin. The RARγ agonist selectivity of a compound can be determined by routine ligand binding assays known to one of skill in the art such as described in C. Apfel et al. *Proc. Nat. Sci. Acad.* (*USA*), 89:7129-7133 (1992); M. Teng et al., *J. Med. Chem.*, 40:2445-2451 (1997); and PCT Publication WO1996030009.

RAR agonists disclosed herein may be used for promoting the repair of damaged tissue, reduce inflammation, increase dermal homeostasis, increase fibro proliferation and decrease microvascular dysfunction. Treatment with RAR agonists, particularly, RARγ selective agonist is useful to promote repair of elastin deposition and tissue repair. RAR selective agonists may also be administered to modulate cell proliferation and cellular differentiation; promote deposition of collagen; activate bone collagen and bone union; stimulate fibroblast activation; stimulate neovascularization; promote elastin formation; up-regulate the plasminogen activator system; increase epidermal proliferation and thickness; increase pro-collagen synthesis; decrease matrix metalloproteinase activity; induce corneal tissue healing; improve functioning of the upper-digestive system; and treat chronically damaged or atrophic skin.

RAR selective agonists may also promote the formation of granulation tissue, collagen deposition and lesion contraction leading to enhanced rate of healing and increased tensile strength of abrasion.

RAR selective agonists may also be useful for treating wrinkling as an incident of aging and actinic damage, normalization of the production of sebum, the reduction of enlarged pores, promoting the rate of wound healing, limiting of scar tissue formation during healing and the like.

In certain embodiments, compositions of the present invention can decrease the amount of internal oxidation and/or external oxidative damage in a cell. In other aspects, the compositions can increase collagen synthesis in a cell. The compositions can also reduce skin inflammation, such as by reducing inflammatory cytokine production in a cell. Non-limiting examples of such cells include human epidermal keratinocyte, human fibroblast dermal cell, human melanocytes, three dimensional human cell-derived in vitro tissue equivalents comprising human keratinocytes, human fibroblasts, or human melanocytes, or any combination thereof (e.g., combination of human keratinocytes and human fibroblasts or a combination of human keratinocytes and human melanocytes).

The method can also include topically applying an amount effective to: increase the stratum corneum turnover rate of the skin; increase collagen synthesis in fibroblasts; increase cellular anti-oxidant defense mechanisms (e.g., exogenous additions of antioxidants can bolster, replenish, or prevent the loss of cellular antioxidants such as catalase and glutathione in skin cells (e.g., keratinocytes, melanocytes, langerhans cells, etc.) which will reduce or prevent oxidative damage to the skin, cellular, proteins, and lipids); inhibit melanin production in melanocytes; reduce or prevent oxidative damage to skin (including reducing the amount lipid peroxides and/or protein oxidation in the skin).

In one aspect, the invention provides a method of treating a disease in a subject comprising administering to the subject a therapeutically effective amount of a RAR selective agonist as disclosed herein. In one aspect, the invention provides a method of treating a disease in a subject comprising administering to the subject a formulation comprising a therapeutically effective amount of a RAR selective as disclosed herein.

In some embodiments, a method of treating a disease in a subject comprises (a) diagnosing the subject as experiencing the disease and (b) administering to the subject a therapeutically effective amount of a RAR selective agonist as disclosed herein. In some embodiments, the invention provides a method of treating a disease in a subject comprising (a) diagnosing the subject as experiencing the disease and (b) administering to the subject a formulation comprising a therapeutically effective amount of a RAR selective agonist as disclosed herein. In exemplary embodiments, the disease is treated.

In some embodiments, a method of preparing a medicament comprises (a) measuring in vitro the quantity of a marker for a disease in a sample derived from a subject experiencing the disease and (b) preparing a RAR selective agonist as disclosed herein in an amount effective for treating (or preventing) the disease. In some embodiments, a method of preparing a medicament comprises (a) measuring in vitro the quantity of a marker for a disease in a sample derived from a subject experiencing the disease and (b) preparing a formulation comprising a RAR selective agonist as disclosed herein in an amount effective for treating (or preventing) the disease. The amount effective for treating the disease may be based on the quantity of the marker that was measured.

In another aspect, the invention provides use of a RAR selective agonist in the manufacture of a medicament for the treatment of a disease. In another aspect, the invention provides use of a formulation comprising a RAR selective agonist in the manufacture of a medicament for the treatment of a disease.

In another aspect, the invention provides use of a RAR selective agonist in the manufacture of a medicament for the prevention of a disease. In another aspect, the invention provides use of a formulation comprising a RAR selective agonist in the manufacture of a medicament for the prevention of a disease.

In one aspect, the invention provides a method of inducing a medically beneficial effect in a subject comprising administering to the subject a therapeutically effective amount of a RAR selective agonist as disclosed herein. In one aspect, the invention provides a method of inducing a medically beneficial effect in a subject comprising administering to the subject a formulation comprising a therapeutically effective amount of a RAR selective agonist as disclosed herein.

In some embodiments, a method of inducing a medically beneficial effect in a subject comprises (a) diagnosing the subject as needing or being capable of benefiting from the medically beneficial effect and (b) administering to the subject a therapeutically effective amount of a RAR selective agonist as disclosed herein. In some embodiments, the invention provides a method of inducing a medically beneficial effect in a subject comprising (a) diagnosing the subject as needing or being capable of benefiting from the medically beneficial effect and (b) administering to the subject a formulation comprising a therapeutically effective amount of a RAR selective agonist as disclosed herein.

In some embodiments, a method of preparing a medicament comprises (a) measuring in vitro the quantity of a marker for a medical state in a sample derived from a subject needing or being capable of benefiting from a medically beneficial effect and (b) preparing a RAR selective agonist as disclosed herein in an amount effective for inducing the medically beneficial effect. In some embodiments, the invention provides a method of treating a disease in a subject comprising (a) measuring in vitro the quantity of a marker for a medical state in a sample derived from a subject needing or being capable of benefiting from a medically beneficial effect and (b) preparing a formulation of a RAR selective agonist as disclosed herein in an amount effective for inducing the medically beneficial effect. The amount effective for inducing the medically beneficial effect may be based on the quantity of the marker that was measured. The medical state may one demonstrating that a subject needs or is capable of benefiting from a medically beneficial effect.

In another aspect, the invention provides use of a RAR selective agonist in the manufacture of a medicament for inducing a medically beneficial effect. In another aspect, the invention provides use of a formulation of a RAR selective agonist in the manufacture of a medicament for inducing a medically beneficial effect.

The diseases referred to in the compositions and methods described herein herein can be any disease that is effectively treated or prevented by administering a RAR selective agonist or formulation thereof to a subject experiencing the disease. The subject may exhibit one or more symptoms of the disease, including changed levels of biomarkers whose varied concentration compared to concentrations in subjects not experiencing the disease provide an indication that the subject may benefit from a RAR selective agonist or formulation thereof. Exemplary diseases are described below and throughout the present disclosure. In some embodiments, the disease is not diabetic ulcer.

In some embodiments, the disease is a metabolic disease. In some embodiments, the disease is a metabolic disease other than diabetic ulcer. In some embodiments, the metabolic disease is metabolic syndrome. Metabolic syndrome is a complex disease, characterized by the American Heart Association by the following abnormalities: abdominal obesity, atherogenic dyslipidemia, hypertension, insulin resistance with or without glucose intolerance, proinflammatory state and prothrombotic state (Grundy et al., Circulation, 2004, 109: 433-438). It is generally recognized in the art that people with three or more of the above symptoms can be considered to have metabolic syndrome. People with the metabolic syndrome are at increased risk of a cardiovascular disease, such as coronary heart disease or other diseases related to plaque buildups in artery walls (e.g., stroke and peripheral vascular disease) and/or Type II diabetes. The term "metabolic syndrome" as used herein refers to a disease characterized by at least three of the following abnormalities: abdominal obesity, atherogenic dyslipidemia, hypertension, insulin resistance with or without glucose intolerance, proinflammatory or inflammation state and prothrombotic state. The treatment or prevention of metabolic syndrome by administration of a RAR selective agonist or a formulation thereof can be achieved by treating or preventing any one or more of these abnormalities or by treating or preventing any one or more symptoms or conditions associated with metabolic syndrome. Exemplary symptoms and conditions associated with metabolic syndrome include hyperglycemia, hyperinsulinemia, hyperlipidemia, impaired glucose metabolism, diabetic retinopathy, macular degeneration, cataracts, diabetic nephropathy, glomerulosclerosis, diabetic neuropathy, erectile dysfunction, premenstrual syndrome, vascular restenosis, and/or ulcerative colitis, angina pectoris, myocardial infarction, stroke, skin and/or connective tissue disorders, metabolic acidosis, arthritis, osteoporosis and conditions of impaired glucose tolerance. In some embodiments, the symptom or condition associated with metabolic syndrome is diabetes or cardiovascular disease.

In some embodiments, the disease is diabetes. Diabetes is characterized by high blood sugar, and may result from the body's failure to produce insulin (Type 1) or from insulin resistance, a condition in which cells fail to use insulin properly, sometimes combined with an absolute insulin deficiency (Type 2). Any known method can be used diagnose diabetes, including, for example, measurement of glucose levels in the blood during an overnight fast and measurement of the body's ability to appropriately handle the excess sugar presented after drinking a high glucose drink.

In some embodiments, the disease is a diabetic complication. A diabetic complication refers to a pathological process or event occurring during diabetes that is not an essential part of the disease. In some embodiments, it may result from the disease, and in some embodiments, it may result from independent causes. In exemplary embodiments, the diabetic complication affects the skin but is not an ulcer. Examples include a bacterial infection, fungal infection, itching, diabetic dermopathy, necrobiosis lipoidica diabeticorum, atherosclerosis, diabetic blisters, eruptive xanthomatosis, digital sclerosis, disseminated granuloma annulare, acathosis nigricans and calluses. Other diabetic complications include diabetic angiopathy and diabetic neuropathy. In some embodiments, the disease is not a diabetic complication. In some embodiments, the disease is not a diabetic ulcer. In some embodiments, the disease is not a foot ulcer, in particular, not a diabetic foot ulcer. In some embodiments, the disease is not a leg ulcer, in particular, not a diabetic leg ulcer. In some embodiments, the disease is a metabolic disease other than diabetic ulcer.

In some embodiments, the disease is a carcinoma. A carcinoma refers to a cancer that begins in a tissue that lines a surface of the body and is generally tumor tissue derived from epithelial cells. Carcinoma growths tend to infiltrate the surrounding tissues and give rise to metastases.

In some embodiments, the disease is a basal cell carcinoma. BCC arises from the basal cells of the epidermis and its appendages. It is characterised by slow local growth capable of causing extensive tissue damage resulting in loss of organ function and disfigurement. The most common etiological factor in BCC is exposure to ultraviolet light (UV). Consequently, areas of skin with high levels of UV exposure, such as the head or neck, are most commonly affected. A number of factors can lead to the development of multiple basal cell carcinoma (MBCC) including conditions such as nevoid basal cell carcinoma syndrome (NBCCS, also referredto as basal cell nevoid syndrome (BCNS) and Gorlin-Goltz syndrome), xeroderma pigmentosum, immunosuppression due to intensive immunosuppressive therapy administered after organ transplant, or radiation exposure at a young age particularly for the treatment of acne. A RAR selective agonist or formulation thereof can be used to treat or prevent basal cell carcinoma. In some embodiments, the basal cell carcinoma is selected from nodular basal-cell carcinoma (classic basal-cell carcinoma), cystic basal-cell carcinoma, cicatricial basal-cell carcinoma (morpheaform basal-cell carcinoma, morphoeic basal-cell carcinoma), Infiltrative basal-cell carcinoma, micronodular basal-cell carcinoma, superficial basal-cell carcinoma (superficial multicentric basal-cell carcinoma), pigmented basal-cell carcinoma, rodent ulcer (Jacobi ulcer), fibroepithelioma of Pinkus, polypoid basal-cell carcinoma, pore-like basal-cell carcinoma and aberrant basal-cell carcinoma.

In some embodiments, the disease is a squamous cell carcinoma. Squamous cell carcinoma arises from the epidermis and resembles the squamous cells that comprise most of the upper layers of skin. Squamous cell cancers may occur on all areas of the body including the mucous membranes, but are most common in areas exposed to the sun. Metastasing squamous cell carcinomas most often arise on sites of chronic inflammatory skin conditions or on the mucous membranes or lips. It has been reported that in patients with psoriasis treated with psoralen-UVA, systemic retinoid use reduced SCC risk but did not significantly alter basal cell carcinoma incidence. Nijsten et al., J Am Acad Dermatol 2003, 49: 644-50. Thus, a RAR selective agonist or formulation thereof can be used to treat or prevent squamous cell carcinoma. In some embodiments, the squamous cell carcinoma is selected from papillary carcinoma, verrucous squamous cell carcinoma, papillary squamous cell carcinoma, squamous cell carcinoma, large cell keratinizing squamous cell carcinoma, large cell keratinizing squamous cell carcinoma, small cell keratinizing squamous cell carcinoma, spindle cell squamous cell carcinoma, adenoid/pseudoglandular squamous cell carcinoma, intraepidermal squamous cell carcinoma and lymphoepithelial carcinoma.

In some embodiments, the disease is leukemia. Leukemia is a form of cancer that begins in the blood-forming cells of the bone marrow and is associated with an excess of abnormal white blood cells in the blood. Acute leukemia is a rapidly progressing disease that results in the massive accumulation of immature, functionless cells (blasts) in the marrow and blood. Chronic leukemia, by contrast, progresses more slowly and leads to unregulated proliferation and hence marked overexpansion of a spectrum of mature (differentiated) cells. RAR selective agonist or formulation thereof can be used to treat or prevent leukemia. In some embodiments, leukemia is selected from myeloid leukemia, lymphocytic leukemia, chronic leukemia (both chronic myeloid leukemia (CML) and chronic lymphocytic leukemia (CLL)), erythroleukemia, thrombocythemia, myelodysplastic syndromes (MDS), acute myeloid leukemia (AML) and acute lymphocytic leukemia (ALL).

In some embodiments, the disease is a cardiovascular disease. The term "cardiovascular disease" includes any disease, disorder or pathological state or condition that involves the heart and/or blood vessels, arteries and veins (vascular disease). A cardiovascular disorder can be caused by an imbalance in arterial pressure, a malfunction of the heart, or an occlusion of a blood vessel, e.g., by a thrombus. A cardiovascular disorder includes, but is not limited to disorders such as arterial disease, atheroma, arteriosclerosis, atherosclerosis, stroke, cardiac hypertrophy, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, valvular disease, including but not limited to, valvular degeneration caused by calcification, rheumatic heart disease, endocarditis, or complications of artificial valves; atrial fibrillation, long-QT syndrome, congestive heart failure, sinus node dysfunction, angina, heart failure, hypertension, atrial fibrillation, atrial flutter, pericardial disease, including but not limited to, pericardial effusion and pericarditis; cardiomyopathies, e.g., dilated cardiomyopathy or idiopathic cardiomyopathy, myocardial infarction, coronary artery disease, coronary heart disease, coronary artery spasm, ischemic disease, transient ischemic attack (TIA), arrhythmia, sudden cardiac death, and cardiovascular developmental disorders (e.g., arteriovenous malformations, arteriovenous fistulae, raynaud's syndrome, neurogenic thoracic outlet syndrome, causalgia/reflex sympathetic dystrophy, hemangioma, aneurysm (e.g., aortic aneurysm), cavernous angioma, aortic valve stenosis, atrial septal defects, atrioventricular canal, coarctation of the aorta, ebsteins anomaly, hypoplastic left heart syndrome, interruption of the aortic arch, mitral valve prolapse, ductus arteriosus, patent foramen ovale, partial anomalous pulmonary venous return, pulmonary atresia with ventricular septal defect, pulmonary atresia without ventricular septal defect, persistance of the fetal circulation, pulmonary valve stenosis, single ventricle, total anomalous pulmonary venous return, transposition of the great vessels, tricuspid atresia, truncus arteriosus, ventricular septal defects), cardiopericarditis, peripheral vascular disease, venous thromoembolism and pulmonary embolism, infection or inflammation of the heart and/or blood vessels, arteries and veins, as well as valvular, vascular and clotting problems, insufficiencies and disorders.

In some embodiments, the disease is an endocrine disease. An endocrine disease is typically characterized by disregulated hormone release (a productive pituitary adenoma), inappropriate response to signaling (hypothyroidism), lack of a gland (diabetes mellitus type 1, diminished erythropoiesis in chronic renal failure), or structural enlargement in a critical site such as the thyroid (toxic multinodular goitre). Hypofunction of endocrine glands can occur as a result of loss of reserve, hyposecretion, agenesis, atrophy, or active destruction. Hyperfunction can occur as a result of hypersecretion, loss of suppression, hyperplastic or neoplastic change, or hyperstimulation. Endocrinopathies are classified as primary, secondary, or tertiary. Primary endocrine disease inhibits the action of downstream glands. Secondary endocrine disease is indicative of a problem with the pituitary gland. Tertiary endocrine disease is associated with dysfunction of the hypothalamus and its releasing hormones. Endocrine diseases generally affect the system of glands that secrete hormones directly into the bloodstream. Organs such as the kidney, liver, heart and gonads have secondary endocrine functions, and thus certain endocrine diseases may also involve disorders of these organs. Classes of endocrine diseases may include, for example, adrenal disorders, glucose homeostasis disorders, calcium homeostasis disorders, metabolic bone disease, pituitary gland disorders, sex hormone disorders and endocrine gland tumors. Examples of endocrine disease include conditions such as adrenal insufficiency (e.g., Addison's disease, mineralocorticoid deficiencies), adrenal hormone excess (e.g., Conn's syndrome, Cushing's syndrome, GRA/Glucocorticoid remediable aldosteronism, pheochromocytoma), congenital adrenal hyperplasia (adrenogenital syndrome), adrenocortical carcinoma, diabetes mellitus (e.g., type 1 diabetes, type 2 diabetes, gestational diabetes, mature onset diabetes), hypoglycemia (e.g., idiopathic hypoglycemia, insulinoma), glucagonoma, thyroiditis (e.g., Hashimoto's thyroiditis), thyroid cancer, parathyroid gland disorders (e.g., primary hyperparathyroidism, secondary hyperparathyroidism, tertiary hyperparathyroidism, hypoparathyroidism, pseudohypoparathyroidism), osteoporosis, osteitis deformans (Paget's disease of bone), rickets and osteomalacia, posterior pituitary disorder (e.g., diabetes insipidus), anterior pituitary disorder (e.g., hypopituitarism or panhypopituitarism, pituitary tumors (such as pituitary adenomas, prolactinoma or hyperprolactinemia, acromegaly, gigantism, Cushing's disease), sex development or intersex disorders (e.g., hermaphroditism, gonadal dysgenesis, androgen insensitivity syndromes, hypogonadism (gonadotropin deficiency), Kallmann syndrome, Klinefelter syndrome, Turner syndrome, ovarian failure (also known as premature menopause), testicular failure, gender identity disorder, disorders of puberty (e.g., delayed puberty, precocious puberty), menstrual function or fertility disorders (e.g., amenorrhea, polycystic ovary syndrome), multiple endocrine neoplasia (e.g., MEN type 1, MEN type 2a, MEN type 2b) and carcinoid syndrome, thyroid disease, and obesity.

In some embodiments, the disease is a neurological disease. In exemplary embodiments, the disease is Alzheimer's disease Alzheimer's disease is characterized by plaques containing amyloid-β (Aβ) peptide and neuronal tangles. It has been hypothesized that late onset Alzheimer's disease (AD) is influenced by the availability in brain of retinoic acid (RA), the final product of the vitamin A (retinoid) metabolic cascade. Goodman & Pardee, Proc Natl Acad Sci USA, 2003 Mar. 4; 100: 2901-2905. The retinoid signalling pathway is mediated by retinoic acid (RA) receptors (RARs) and retinoid X receptors (RXRs), both of which have three types, α, β and γ, and various isoforms. Bastien & Rochette-Egly, Gene, 2004, 328: 1-16. Jarvis et al., European Journal of Neuroscience, 2010, 32: 1246-1255, have reported that RARα agonists have therapeutic potential for the treatment of AD. A RAR selective agonist or formulation thereof as disclosed herein may thus be administered to a subject in order to treat or prevent Alzheimer's disease.

In some embodiments, the disease is heterotrophic ossification. In subjects suffering from heterotrophic ossification, ectopic bone forms within muscles and connective tissues and near blood vessels or nerves. The pathogenesis of this disease is not completely understood, but it is thought that inciting events, such as trauma, surgery (especially invasive surgery such as knee replacement), deep burns or protracted immobilization, induce local inflammation, which is followed by the recruitment of skeletal progenitor cells that differentiate into chondrocytes, undergo hypertrophy and are replaced by endochondral bone. Shimono et al., Nature Medicine, 2011, 17: 454-461. Shimono et al. have reported that heterotopic ossification was essentially prevented in mice receiving a nuclear retinoic acid receptor-γ (RAR-γ) agonist. Accordingly, a RAR selective agonist or formulation thereof as disclosed herein may thus be administered to a subject in order to treat or prevent heterotrophic ossification.

In some embodiments, the disease is a topical disease other than diabetic ulcer. In some embodiments, the topical disease is selected from dermal atrophy, hyperpigmentation, hypopigmentation, dermal hypoplasia, epidermal hypoplasia, keratoses, ichthyoses, follicular disorders, benign epithelial tumors, perforated dematoses, keratinization disorders and chronic lesion caused by reduced RARγ expression.

In some embodiments, the disease is a skin condition. Non-limiting examples of skin conditions include pruritus, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, impetigo, erysipelas, erythrasma, eczema, and other inflammatory skin conditions. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition.

In some embodiments, the disease is an ocular surface disease. It is well established that the cornea and the conjunctiva have an absolute requirement for vitamin A (retinol), which acts through its metabolites such as retinaldehyde, which forms the visual chromophore, and retinoic acids, which regulate gene expression. Nezzar et al., Molecular Vision, 2007, 13: 1641-1650. Diseases such as keratinization, xerophthalmia, keratomalacia, ulceration, epithelial squamous metaplasia and a deficiency of conjunctival goblet cells may result from abnormal differentiation of the ocular surface due to vitamin A deficiency. A RAR selective agonist or formulation thereof (particularly a topical formulation) as disclosed herein may thus be administered to a subject in order to treat or prevent any of these ocular surface diseases, and additionally may be useful for the treatment or prevention of dry eye or corneal epithelial wounds.

In some embodiments, the disease targeted by the methods, compounds and formulations described herein is a disease selected from skin lesion, acne vulgaris, cystic acne, psoriasis, ichthyoses (e.g., ichthyosis hystrix, epidermolytic hyperkeratosis, and lamellar ichthyosis), follicular disorders (e.g., pseudofolliculites, senile comedones, nevus comidonicas, and trichostatis spinulosa), benign epithelial tumors (e.g., flat warts, trichoepithelioma, and molluscum contagiosum), perforated dematoses (e.g., elastosis perforans seripiginosa and Kyrles disease), and disorders of keratinization (e.g., Dariers disease, keratoderma, hyperkeratosis plantaris, pityriasis rubra pilaris, lichen planus acanthosis nigricans, and psoriasis).

In some embodiments, the treatment or prevention of certain diseases is excluded. Any disease disclosed herein may be excluded. For example, in some embodiments, the disease is not one or more diseases selected from an epithelial lesion; light- and age-damaged skin; skin lesion; acne (e.g., acne vulgaris, cystic acne); psoriasis; a tumor or precancerous change of the mucous membrane in the mouth, tongue, larynx, esophagus, bladder, cervix or colon; and emphysema and associated pulmonary diseases. In some embodiments, the treatment of a trauma or of an induced wound is excluded; examples include burns and surgical wounds.

In one aspect, the invention provides a method of inducing a medically beneficial effect (such as inducing bone collagen formation) in a subject comprising administering to the subject a therapeutically effective amount of a RAR selective agonist or a formulation comprising a RAR selective agonist. RAR selective agonists can thus be administered to subjects who are not suffering from disease.

In a particular embodiment, there is disclosed a method of reducing the appearance of a nonpathological skin condition comprising topically applying any one of the compositions described in this specification to the skin condition, wherein topical application of the composition to skin condition reduces the appearance of the skin condition. In some embodiments, the skin condition is a fine line or wrinkle, uneven skin tone, or an age spot. The skin condition can be located on facial skin, arm skin, leg skin, chest skin, abdomen skin, back skin etc.

In yet another embodiment, there is disclosed a method of increasing the firmness of skin comprising topically applying any one of the compositions described in this specification to skin in need thereof (a non-limiting example of which can be sagging skin, aged skin, skin that has reduced elasticity, skin that has skin cells having inadequate amounts of collage, fibronectin, or laminin or all of such proteins, etc.), wherein topical application of the composition to skin increases the firmness of skin. The composition can be used on facial skin, arm skin, leg skin, chest skin, abdomen skin, back skin, etc.

In still another embodiment there is disclosed a method of increasing collagen, fibronectin, or laminin production in a skin cell comprising topically applying any one of the compositions disclosed in this specification to a skin cell that is in need of collagen, fibronectin, or laminin production, wherein the topical application of the composition to the skin cell increases collagen, fibronectin, or laminin production in the skin cell. In certain aspects, collagen, fibronectin, and laminin production are increased in the skin cell.

In one aspect, the invention provides a method of inducing bone collagen formation in a subject, the method comprising administering to the subject a RAR selective agonist. In one aspect, the invention provides a method of inducing bone collagen formation in a subject, the method comprising administering to the subject formulation comprising a RAR selective agonist. The effect of retinoic acid on development and healing of osseous tissues, as well as on maintenance of normal skeletal growth and remodeling, has been well established. Sela et al., Inflamm. Res., 2000, 49: 679-683. Physiological doses of retinoic acid induce collagen gene expression in approximately one third of the cells treated with it, and increase alkaline phosphatase levels. Pacifici et al., Exper. Cell Res., 1991, 195: 38-46. Studies have suggested that retinoic acid either directly increases the synthesis of collagen, or reduces degradation of certain types of pro-collagen. Sela, supra. Accordingly, a RAR selective agonist or formulation thereof as disclosed herein may thus be administered to a subject in order to induce bone collagen formation.

A "subject" in the context of the present invention is an animal, preferably a mammal. The mammal can be a human, non-human primate, mouse, rat, dog, cat, horse, or cow, but are not limited to these examples. In various exemplary embodiments, a subject is human and may be referred to as a "patient". Mammals other than humans can be advantageously used as subjects that represent animal models of a disease or for veterinarian applications. A subject can be one who has been previously diagnosed or identified as having a disease, and optionally has already undergone, or is undergoing, a therapeutic intervention for a disease. Alternatively, a subject can also be one who has not been previously diagnosed as having a disease. For example, a subject can be one who exhibits one or more risk factors for a disease, or one who does not exhibit a disease risk factor, or one who is asymptomatic for a disease. A subject can also be one who is suffering from or at risk of developing a disease. In certain embodiments, the subject can be already undergoing therapy or can be a candidate for therapy. In exemplary embodiments, the subject is generally one in need of treatment for a disease or has been determined to be in need for treatment of a disease.

Thus, the methods disclosed herein can further comprise identifying a subject as in need of treatment of a disease disclosed herein.

The term "sample" used herein refers to a specimen or culture obtained from a subject and includes fluids, gases and solids including, for example, tissue. In various exemplary embodiments, the sample comprises blood. A sample could be a fluid obtained from a subject including, for example, whole blood or a blood derivative (e.g. serum, plasma, or blood cells), ovarian cyst fluid, ascites, lymphatic, cerebrospinal or interstitial fluid, saliva, mucous, sputum, sweat, urine, or any other secretion, excretion, or other bodily fluids. As will be appreciated by those in the art, virtually any experimental manipulation or sample preparation steps may have been done on the sample. For example, wash steps may be applied to a sample.

The terms "treatment" and "treating" refer to the reduction of the progression, severity and/or duration of a disease or amelioration of one or more symptoms thereof, wherein such reduction and/or amelioration result from the administration of one or more therapies (e.g., a RAR selective agonist or a formulation thereof).

In some aspects, a RAR selective agonist or a formulation thereof is administered for preventing a disease or is used in manufacturing or preparing a medicament for preventing a disease. Such methods may include the same steps performed in methods of treating the disease.

Administration of a RAR selective agonist include topical application of the compound or a formulation thereof to a portion of skin in need of such compound or formulation, wherein topical application reduces or prevents a skin condition when compared to skin that has a skin condition and that has not been treated with the composition, or wherein topical application increases bone collagen formation. The skin can be facial skin or non-facial skin (e.g., arms, legs, hands, chest, back, feet, etc.). Administration of a RAR selective agonist also includes oral administration.

Delivery of the compounds of the present invention to the subject over prolonged periods of time, for example, for periods of one week to one year, may be accomplished by a single administration of a controlled release system containing sufficient active ingredient for the desired release period. Various controlled release systems, such as transdermal patches, devices and alternative dosage forms may be utilized for this purpose. Localization at the site to which delivery of the active ingredient is desired is an additional feature of some controlled release devices, which may prove beneficial in the treatment of certain disorders.

EXAMPLES

The Examples below provide a number of exemplary formulations. In some embodiments, the formulation comprises any of the indicated components at about the weight percentage shown.

Example 1

Table 1 provides exemplary concentrations of ingredients suitable for formulating an ointment.

TABLE 1

| Ingredient | Wt/wt % |
|---|---|
| RAR selective agonist | 0.005% |
| stearyl alcohol | 1% |
| stearic acid | 4% |
| isopropylmyristate | 13% |
| BHT | 0.01% |
| gum xanthan | 1.5% |
| polyoxyl 40 stearate | 2% |
| sorbic acid | 0.1% |
| corn oil | 0.045% |
| filtered water | 78.34% |

Example 2

Table 2 provides exemplary concentrations of ingredients suitable for formulating an ointment.

TABLE 2

| Ingredient | Wt/wt % |
|---|---|
| RAR selective agonist | 0.01% |
| stearyl alcohol | 1% |
| stearic acid | 4% |
| isopropylmyristate | 13% |
| BHT | 0.01% |
| gum xanthan | 1.5% |
| polyoxyl 40 stearate | 2% |
| sorbic acid | 0.1% |
| corn oil | 0.045% |
| filtered water | 78.335% |

Example 3

Table 3 provides exemplary concentrations of ingredients suitable for formulating an ointment.

TABLE 3

| Ingredient | Wt/wt % |
|---|---|
| RAR selective agonist | 0.05% |
| stearyl alcohol | 1% |
| stearic acid | 4% |
| isopropylmyristate | 13% |
| BHT | 0.01% |
| gum xanthan | 1.5% |
| polyoxyl 40 stearate | 2% |
| sorbic acid | 0.1% |
| corn oil | 0.045% |
| filtered water | 78.295% |

Example 4

The following are exemplary embodiments.

Embodiment 1

A method of treating a metabolic disease or a condition associated with the metabolic disease in a subject, wherein the metabolic disease is other than diabetic ulcer, the method comprising: administering to the subject a therapeutically effective amount of a RAR selective agonist, wherein the RAR selective agonist has the structure:

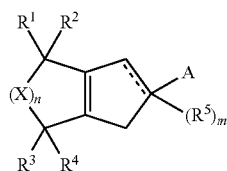

(I)

wherein the dotted bond is either present and forms a double bond, or is absent;

$R^1$, $R^2$, $R^3$ and $R^4$ are independently hydrogen or alkyl;

n is 1, 2 or 3;

X is —C($R^8$)($R^9$)— for n=1, 2 or 3; or X is oxygen for n=1; wherein $R^8$ and $R^9$ are independently hydrogen or alkyl;

$R^5$ is hydrogen, alkyl, alkoxy, alkoxy-alkyl-, alkylthio, alkyl-$NR^{10}$—, alkenyl, alkenyloxy, alkynyl, benzyl, cycloalkyl-alkyl or phenyl-alkyl;

wherein $R^{10}$ is hydrogen or alkyl;

m is 0 when the dotted bond is present; or m is 1 when the dotted bond is absent;

A is a residue of formula:

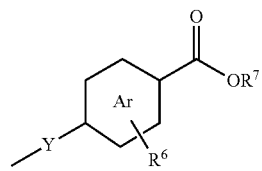

(a)

or of formula:

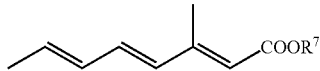

(b)

wherein Ar is phenyl or a heteroarylic ring;
$R^6$ is hydrogen, halogen, alkoxy or hydroxy;
$R^7$ is hydrogen or alkyl; and
Y is —COO—, —OCO—, —CONR$^{10}$—, —NR$^{10}$CO—, —CH═CH—, —C≡C—, —COCH═CH—, —CHOHCH═CH—, —CH$_2$O—, —CH$_2$S—, —CH$_2$SO—, —CH$_2$SO$_2$—, —CH$_2$NR$^{10}$—, —OCH$_2$—, —SCH$_2$—, —SOCH$_2$—, —SO$_2$CH$_2$— or —NR$^{10}$CH$_2$—,
with the proviso that when Y is —OCO—, —NR$^{10}$CO—, —OCH$_2$—, —SCH$_2$—, —SOCH$_2$—, —SO$_2$CH$_2$— or —NR$^{10}$CH$_2$—, $R^5$ is hydrogen, alkyl, alkoxy-alkyl-, alkenyl, alkynyl, benzyl, cycloalkyl-alkyl or phenyl-alkyl;
or a pharmaceutically active salt of carboxylic acids of formula I.

Embodiment 2

The method of embodiment 1 wherein the condition associated with the metabolic disease is selected from hyperglycemia, hyperinsulinemia, hyperlipidemia, impaired glucose metabolism, diabetic retinopathy, macular degeneration, cataracts, diabetic nephropathy, glomerulosclerosis, diabetic neuropathy, erectile dysfunction, premenstrual syndrome, vascular restenosis, ulcerative colitis, angina pectoris, myocardial infarction, stroke, skin or connective tissue disorders, metabolic acidosis, arthritis, osteoporosis, conditions of impaired glucose tolerance, diabetes and cardiovascular disease.

Embodiment 3

A method of treating a topical disease in a subject, wherein the topical disease is selected from skin lesion, acne vulgaris, cystic acne and psoriasis;
the method comprising: administering to the subject a topical formulation comprising a RAR selective agonist,
wherein the RAR selective agonist is about 0.00001% to about 1% wt/wt of the formulation, and
wherein the RAR selective agonist has the structure:

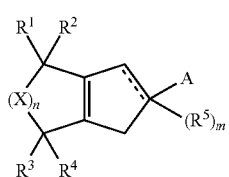

(I)

wherein the dotted bond is either present and forms a double bond, or is absent;
$R^1$, $R^2$, $R^3$ and $R^4$ are independently hydrogen or alkyl;
n is 1, 2 or 3;
X is —C(R$^8$)(R$^9$)— for n=1, 2 or 3; or X is oxygen for n=1;
wherein R$^8$ and R$^9$ are independently hydrogen or alkyl;

$R^5$ is hydrogen, alkyl, alkoxy, alkoxy-alkyl-, alkylthio, alkyl-NR$^{10}$—, alkenyl, alkenyloxy, alkynyl, benzyl, cycloalkyl-alkyl or phenyl-alkyl;
wherein R$^{10}$ is hydrogen or alkyl;
m is 0 when the dotted bond is present; or m is 1 when the dotted bond is absent;
A is a residue of formula:

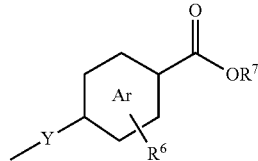

(a)

or of formula:

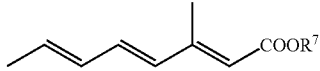

(b)

wherein Ar is phenyl or a heteroarylic ring;
$R^6$ is hydrogen, halogen, alkoxy or hydroxy;
$R^7$ is hydrogen or alkyl; and
Y is —COO—, —OCO—, —CONR$^{10}$—, —NR$^{10}$CO—, —CH═CH—, —C≡C—, —COCH═CH—, —CHOHCH═CH—, —CH$_2$O—, —CH$_2$S—, —CH$_2$SO—, —CH$_2$SO$_2$—, —CH$_2$NR$^{10}$—, —OCH$_2$—, —SCH$_2$—, —SOCH$_2$—, —SO$_2$CH$_2$— or —NR$^{10}$CH$_2$—,
with the proviso that when Y is —OCO—, —NR$^{10}$CO—, —OCH$_2$—, —SCH$_2$—, —SOCH$_2$—, —SO$_2$CH$_2$— or —NR$^{10}$CH$_2$—, $R^5$ is hydrogen, alkyl, alkoxy-alkyl-, alkenyl, alkynyl, benzyl, cycloalkyl-alkyl or phenyl-alkyl;
or a pharmaceutically active salt of carboxylic acids of formula I.

Embodiment 4

A method of inducing bone collagen formation in a subject, the method comprising: administering to the subject a RAR selective agonist having the structure:

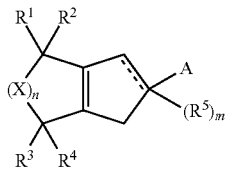

(I)

wherein the dotted bond is either present and forms a double bond, or is absent;
$R^1$, $R^2$, $R^3$ and $R^4$ are independently hydrogen or alkyl;
n is 1, 2 or 3;
X is —C(R$^8$)(R$^9$)— for n=1, 2 or 3; or X is oxygen for n=1;
wherein R$^8$ and R$^9$ are independently hydrogen or alkyl;
$R^5$ is hydrogen, alkyl, alkoxy, alkoxy-alkyl-, alkylthio, alkyl-NR$^{10}$—, alkenyl, alkenyloxy, alkynyl, benzyl, cycloalkyl-alkyl or phenyl-alkyl;

wherein $R^{10}$ is hydrogen or alkyl;

m is 0 when the dotted bond is present; or m is 1 when the dotted bond is absent;

A is a residue of formula:

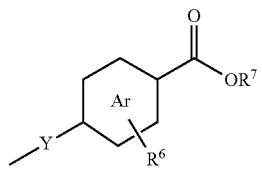

(a)

or of formula:

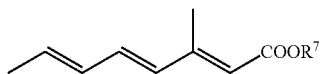

(b)

wherein Ar is phenyl or a heteroarylic ring;

$R^6$ is hydrogen, halogen, alkoxy or hydroxy;

$R^7$ is hydrogen or alkyl; and

Y is —COO—, —OCO—, —CONR$^{10}$—, —NR$^{10}$CO—, —CH═CH—, —C≡C—, —COCH═CH—, —CHOHCH═CH—, —CH$_2$O—, —CH$_2$S—, —CH$_2$SO—, —CH$_2$SO$_2$—, —CH$_2$NR$^{10}$—, —OCH$_2$—, —SCH$_2$—, —SOCH$_2$—, —SO$_2$CH$_2$— or —NR$^{10}$CH$_2$—, with the proviso that when Y is —OCO—, —NR$^{10}$CO—, —OCH$_2$—, —SCH$_2$—, —SOCH$_2$—, —SO$_2$CH$_2$— or —NR$^{10}$CH$_2$—, $R^5$ is hydrogen, alkyl, alkoxy-alkyl-, alkenyl, alkynyl, benzyl, cycloalkyl-alkyl or phenyl-alkyl;

or a pharmaceutically active salt of carboxylic acids of formula I.

Embodiment 5

The method of any of embodiments 1, 2 and 4 wherein the RAR selective agonist is in a formulation comprising:
(a) the RAR selective agonist and
(b) a carrier medium comprising one or more excipients,
wherein the formulation is suitable for topical administration to the subject.

Embodiment 6

The method of any preceding embodiment wherein the RAR selective agonist is administered by applying a cream, ointment, lotion or liquid comprising the RAR selective agonist.

Embodiment 7

The method of any preceding embodiment wherein the RAR selective agonist is in a formulation comprising:
(a) the RAR selective agonist and
(b) a carrier medium comprising one or more excipients,
wherein the RAR selective agonist is about 0.00001 wt % to about 1 wt % of the formulation.

Embodiment 8

The method of any of embodiments 5 and 7 wherein the carrier medium comprises (a) an alcohol;
(b) stearic acid;
(c) isopropylmyristate;
(d) polyoxyl stearate;
(e) butylated hydroxytoluene;
(f) xanthan gum;
(g) sorbic acid;
(h) an oil; and
(i) water.

Embodiment 9

The method of embodiment 8
wherein the alcohol is about 0.5 wt % to about 1.5 wt % of the formulation;
the stearic acid is about 2 wt % to about 7 wt % of the formulation;
the isopropylmyristate is about 6 wt % to about 16 wt % of the formulation; and
the polyoxyl stearate is about 1 wt % to about 6 wt % of the formulation.

Embodiment 10

The method of any of embodiments 8 and 9
wherein the alcohol is about 1 wt % of the formulation;
the stearic acid is about 4 wt % of the formulation;
the isopropylmyristate is about 13 wt % of the formulation;
the butylated hydroxytoluene is about 0.01 wt % of the formulation;
the xanthan gum is about 1.5 wt % of the formulation;
the polyoxyl stearate is about 2 wt % of the formulation;
the sorbic acid is about 0.1 wt % of the formulation;
the oil is about 0.045 wt wt % of the formulation; and
the water is about 78.34 wt % of the formulation.

Embodiment 11

The method of any of embodiments 8-10 wherein the alcohol is stearyl alcohol; the polyoxyl stearate is polyoxyl 40 stearate; or the oil is corn oil.

Embodiment 12

The method of any of embodiments 1, 2 and 4 wherein the RAR selective agonist is in a formulation comprising:
(a) the RAR selective agonist and
(b) a carrier medium comprising one or more excipients,
wherein the formulation is suitable for oral administration to the subject.

Embodiment 13

The method of any preceding embodiment wherein the RAR selective agonist has the structure:

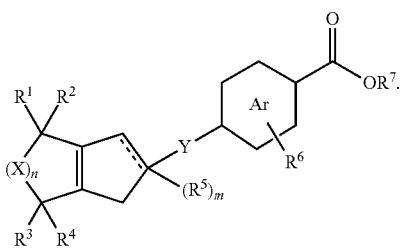

Embodiment 14

The method of any preceding embodiment wherein the RAR selective agonist has the structure

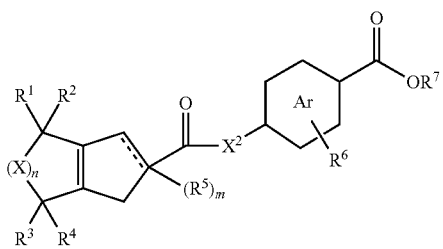

wherein $X^2$ is oxygen or —NH—.

Embodiment 15

The method of embodiment 14 wherein $X^2$ is oxygen and n is 2.

Embodiment 16

The method of any preceding embodiment wherein $R^8$ and $R^9$ are H.

Embodiment 17

The method of any preceding embodiment wherein $R^1$, $R^2$, $R^3$ and $R^4$ are alkyl.

Embodiment 18

A composition comprising:
(a) a RAR selective agonist; and
(b) an analgesic, an anesthetic or an antibiotic,
wherein the RAR selective agonist has the structure:

(I)

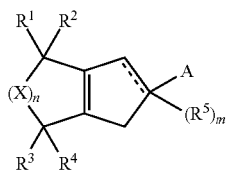

wherein the dotted bond is either present and forms a double bond, or is absent;
$R^1$, $R^2$, $R^3$ and $R^4$ are independently hydrogen or alkyl;
n is 1, 2 or 3;
X is —C($R^8$)($R^9$)— for n=1, 2 or 3; or X is oxygen for n=1; wherein $R^8$ and $R^9$ are independently hydrogen or alkyl;
$R^5$ is hydrogen, alkyl, alkoxy, alkoxy-alkyl-, alkylthio, alkyl-$NR^{10}$—, alkenyl, alkenyloxy, alkynyl, benzyl, cycloalkyl-alkyl or phenyl-alkyl;
wherein $R^{10}$ is hydrogen or alkyl;
m is 0 when the dotted bond is present; or m is 1 when the dotted bond is absent;
A is a residue of formula:

(a)

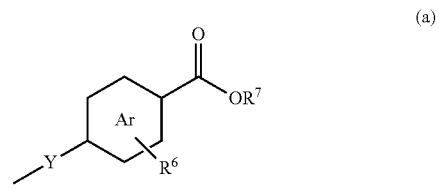

or of formula:

(b)

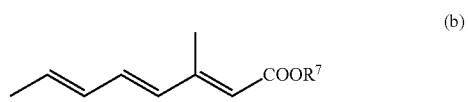

wherein Ar is phenyl or a heteroarylic ring;
$R^6$ is hydrogen, halogen, alkoxy or hydroxy;
$R^7$ is hydrogen or alkyl; and
Y is —COO—, —OCO—, —$CONR^{10}$—, —$NR^{10}CO$—, —CH=CH—, —C≡C—, —COCH=CH—, —CHOHCH=CH—, —$CH_2O$—, —$CH_2S$—, —$CH_2SO$—, —$CH_2SO_2$—, —$CH_2NR^{10}$—, —$OCH_2$—, —$SCH_2$—, —$SOCH_2$—, —$SO_2CH_2$— or —$NR^{10}CH_2$—,
with the proviso that when Y is —OCO—, —$NR^{10}CO$—, —$OCH_2$—, —$SCH_2$—, —$SOCH_2$—, —$SO_2CH_2$— or —$NR^{10}CH_2$—, $R^5$ is hydrogen, alkyl, alkoxy-alkyl-, alkenyl, alkynyl, benzyl, cycloalkyl-alkyl or phenyl-alkyl;
or a pharmaceutically active salt of carboxylic acids of formula I.

Embodiment 19

The composition of embodiment 18 wherein the RAR selective agonist has the structure:

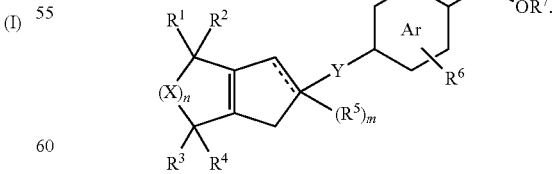

Embodiment 20

The composition of any of embodiments 18 and 19 wherein the RAR selective agonist has the structure

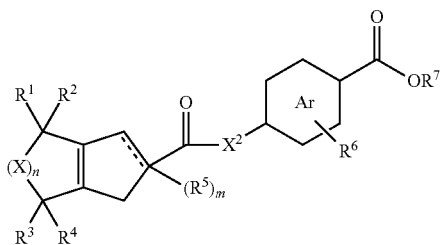

wherein $X^2$ is oxygen or —NH—.

Embodiment 21

The composition of embodiment 20 wherein $X^2$ is oxygen and n is 2.

Embodiment 22

The composition of any of embodiments 18-21 wherein $R^8$ and $R^9$ are H.

Embodiment 23

The composition of any of embodiments 18-22 wherein $R^1$, $R^2$, $R^3$ and $R^4$ are alkyl.

Embodiment 24

The composition of any of embodiments 18-23 further comprising a carrier medium, wherein the composition is a pharmaceutically acceptable formulation.

Embodiment 25

A stent comprising a RAR selective agonist having the structure:

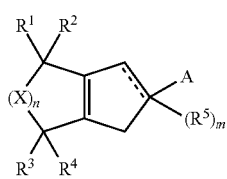
(I)

wherein the dotted bond is either present and forms a double bond, or is absent;
$R^1$, $R^2$, $R^3$ and $R^4$ are independently hydrogen or alkyl;
n is 1, 2 or 3;
X is —C($R^8$)($R^9$)— for n=1, 2 or 3; or X is oxygen for n=1; wherein $R^8$ and $R^9$ are independently hydrogen or alkyl;
$R^5$ is hydrogen, alkyl, alkoxy, alkoxy-alkyl-, alkylthio, alkyl-$NR^{10}$—, alkenyl, alkenyloxy, alkynyl, benzyl, cycloalkyl-alkyl or phenyl-alkyl;
wherein $R^{10}$ is hydrogen or alkyl;
m is 0 when the dotted bond is present; or m is 1 when the dotted bond is absent;

A is a residue of formula:

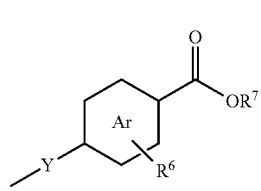
(a)

or of formula:

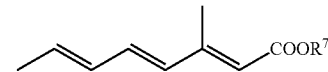
(b)

wherein Ar is phenyl or a heteroarylic ring;
$R^6$ is hydrogen, halogen, alkoxy or hydroxy;
$R^7$ is hydrogen or alkyl; and
Y is —COO—, —OCO—, —$CONR^{10}$—, —$NR^{10}CO$—, —CH═CH—, —C≡C—, —COCH═CH—, —CHOHCH═CH—, —$CH_2O$—, —$CH_2S$—, —$CH_2SO$—, —$CH_2SO_2$—, —$CH_2NR^{10}$—, —$OCH_2$—, —$SCH_2$—, —$SOCH_2$—, —$SO_2CH_2$— or —$NR^{10}CH_2$—,
with the proviso that when Y is —OCO—, —$NR^{10}CO$—, —$OCH_2$—, —$SCH_2$—, —$SOCH_2$—, —$SO_2CH_2$— or —$NR^{10}CH_2$—, $R^5$ is hydrogen, alkyl, alkoxy-alkyl-, alkenyl, alkynyl, benzyl, cycloalkyl-alkyl or phenyl-alkyl;

or a pharmaceutically active salt of carboxylic acids of formula I.

Embodiment 26

The stent of embodiment 25 wherein the RAR selective agonist has the structure:

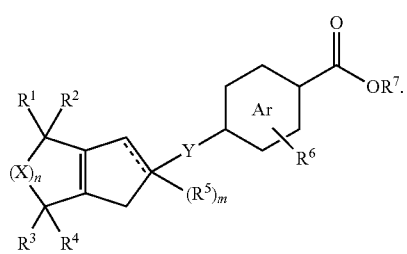

Embodiment 27

The stent of any of embodiments 25 and 26 wherein the RAR selective agonist has the structure

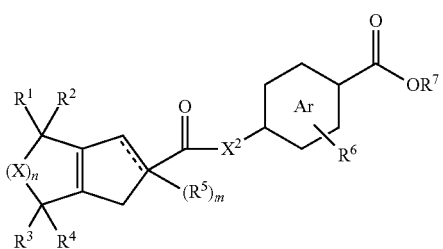

wherein X² is oxygen or —NH—.

Embodiment 28

The stent of embodiment 27 wherein X² is oxygen and n is 2.

Embodiment 29

The stent of any of embodiments 25-28 wherein $R^8$ and $R^9$ are H.

Embodiment 30

The stent of any of embodiments 25-29 wherein $R^1$, $R^2$, $R^3$ and $R^4$ are alkyl.

DEFINITION AND INCORPORATION BY REFERENCE

The articles "a," "an" and "the" as used herein do not exclude a plural number of the referent, unless context clearly dictates otherwise. The conjunction "or" is not mutually exclusive, unless context clearly dictates otherwise. The term "include" refers to nonexhaustive examples.

All references, publications, patent applications, issued patents, accession records, databases, websites and document urls cited herein are incorporated by reference in their entirety for all purposes.

I claim:

1. A method of treating acne vulgaris, the method comprising: administering to a subject a topical formulation comprising a single active ingredient, wherein the active ingredient consists of a RAR selective agonist, wherein the RAR selective agonist is not more than 0.005% of the formulation, and wherein the RAR selective agonist has the structure:

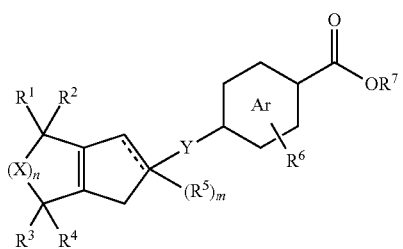

wherein the dotted bond is either present and forms a double bond, or is absent;
$R^1$, $R^2$, $R^3$ and $R^4$ are independently hydrogen or alkyl;
n is 1, 2 or 3;
X is —C($R^8$)($R^9$)— for n=1, 2 or 3; or X is oxygen for n=1;
wherein $R^8$ and $R^9$ are independently hydrogen or alkyl;
$R^5$ is hydrogen, alkyl, alkoxy, alkoxy-alkyl-, alkylthio, alkyl-$NR^{10}$—, alkenyl, alkenyloxy, alkynyl, benzyl, cycloalkyl-alkyl or phenyl-alkyl;
wherein $R^{10}$ is hydrogen or alkyl;
m is 0 when the dotted bond is present; or m is 1 when the dotted bond is absent;
wherein Ar is phenyl or a heteroarylic ring;
$R^6$ is hydrogen, halogen, alkoxy or hydroxy;
$R^7$ is hydrogen or alkyl; and
Y is —COO—, —OCO—, —$CONR^{10}$—, —$NR^{10}CO$—, —CH=CH—, —C≡C—, —COCH=CH—, —CHOHCH=CH—, —$CH_2O$—, —$CH_2S$—, —$CH_2SO$—, —$CH_2SO_2$—, —$CH_2NR^{10}$—, —OC $H_2$—, —$SCH_2$—, —$SOCH_2$—, —$SO_2CH_2$— or —$NR^{10}CH_2$—,
with the proviso that when Y is —OCO—, —$NR^{10}CO$—, —$OCH_2$—, —$SCH_2$—, —$SOCH_2$—, —$SO_2CH_2$— or —$NR^{10}CH_2$—, $R^5$ is hydrogen, alkyl, alkoxy-alkyl-, alkenyl, alkynyl, benzyl, cycloaslkyl-alkyl or phenyl-alkyl;
or a pharmaceutically active salt of carboxylic acids of formula I.

2. The method of claim 1 wherein the RAR selective agonist is administered by applying a cream, ointment, lotion or liquid comprising the RAR selective agonist.

3. The method of claim 1 wherein $R^8$ and $R^9$ are H.

4. The method of claim 1 wherein $R^1$, $R^2$, $R^3$ and $R^4$ are alkyl.

5. The method of claim 1, wherein
$R_1$, $R_2$, $R_3$, and $R_4$ are each methyl,
$X_n$ is —$CH_2$—$CH_2$—,
$R_5$ is —$CH_2$—$CH_2$—$CH_2$—$CH_2$—$CH_3$,
Y is —COO—, and
$R_6$ and $R_7$ are each is H.

6. The method of claim 1, wherein
$R^1$, $R^2$, $R^3$ and $R^4$ are independently hydrogen or alkyl;
n is 1 or 2;
X is —C($R^8$)($R^9$)— for n=1 or 2; or X is oxygen for n=1;
wherein $R^8$ and $R^9$ are independently hydrogen or alkyl; and
$R^5$ is hydrogen, alkyl, alkoxy, alkoxy-alkyl-, alkylthio, alkyl-$NR^{10}$—, alkenyl, alkenyloxy, alkynyl;
wherein $R^{10}$ is hydrogen or alkyl.

7. The method of claim 1, wherein
$R^1$, $R^2$, $R^3$ and $R^4$ are independently hydrogen or alkyl;
n is 1 or 2;
X is —C($R^8$)($R^9$)— for n=1 or 2; or X is oxygen for n=1;
wherein $R^8$ and $R^9$ are independently hydrogen or alkyl; and
$R^5$ is hydrogen, alkyl, alkylthio, alkyl-$NR^{10}$—, alkenyl, alkynyl;
wherein $R^{10}$ is hydrogen or alkyl.

8. The method of claim 1, wherein
$R^1$, $R^2$, $R^3$ and $R^4$ are independently hydrogen or alkyl;
n is 2;
X is —C($R^8$)($R^9$)— for n=2;
wherein $R^8$ and $R^9$ are independently hydrogen or alkyl; and
$R^5$ is hydrogen, alkyl, alkoxy, alkoxy-alkyl-, alkylthio, alkyl-$NR^{10}$—, alkenyl, alkenyloxy, alkynyl;
wherein $R^{10}$ is hydrogen or alkyl.

9. The method of claim 1, wherein
$R^1$, $R^2$, $R^3$ and $R^4$ are independently hydrogen or alkyl;
n is 2;
X is —$C(R^8)(R^9)$— for n=2;
   wherein $R^8$ and $R^9$ are independently hydrogen or alkyl; and
$R^5$ is hydrogen, alkyl, alkylthio, alkyl-$NR^{10}$—, alkenyl, alkynyl;
   wherein $R^{10}$ is hydrogen or alkyl.

10. The method of claim 1, wherein
$R^1$, $R^2$, $R^3$ and $R^4$ are independently hydrogen or alkyl;
n is 2;
X is —$C(R^8)(R^9)$— for n=2;
   wherein $R^8$ and $R^9$ are independently hydrogen or alkyl;
$R^5$ is hydrogen, alkyl, alkoxy, alkoxy-alkyl-, alkylthio, alkyl-$NR^{10}$—, alkenyl, alkenyloxy, alkynyl;
   wherein $R^{10}$ is hydrogen or alkyl; and
Y is —COO—, —OCO—, —$CONR^{10}$—, —$NR^{10}CO$—, —CH=CH—, —C≡C—, —$CH_2O$—, —$CH_2S$—, —$CH_2SO$—, —$CH_2SO_2$—, —$CH_2NR^{10}$—, —$OCH_2$—, —$SCH_2$—, —$SOCH_2$—, —$SO_2CH_2$— or —$NR^{10}CH_2$—,
with the proviso that when Y is —OCO—, —$NR^{10}CO$—, —$OCH_2$—, —$SCH_2$—, —$SOCH_2$—, —$SO_2CH_2$— or —$NR^{10}CH_2$—, $R^5$ is hydrogen, alkyl, alkoxy-alkyl-, alkenyl, alkynyl.

11. The method of claim 1, wherein
$R^1$, $R^2$, $R^3$ and $R^4$ are independently hydrogen or alkyl;
n is 2;
X is —$C(R^8)(R^9)$— for n=2;
   wherein $R^8$ and $R^9$ are independently hydrogen or alkyl; and
$R^5$ is hydrogen, alkyl, alkylthio, alkyl-$NR^{10}$—, alkenyl, alkynyl;
   wherein $R^{10}$ is hydrogen or alkyl; and
Y is —COO—, —OCO—, —$CONR^{10}$—, —$NR^{10}CO$—, —CH=CH—, —C≡C—, —$CH_2O$—, —$CH_2S$—, —$CH_2SO$—, —$CH_2SO_2$—, —$CH_2NR^{10}$—, —$OCH_2$—, —$SCH_2$—, —$SOCH_2$—, —$SO_2CH_2$— or —$NR^{10}CH_2$—,
with the proviso that when Y is —OCO—, —$NR^{10}CO$—, —$OCH_2$—, —$SCH_2$—, —$SOCH_2$—, —$SO_2CH_2$— or —$NR^{10}CH_2$—, $R^5$ is hydrogen, alkyl, alkenyl, alkynyl.

* * * * *